（12）United States Patent
Dobrokhotov et al.

(10) Patent No.: US 11,275,051 B2
(45) Date of Patent: Mar. 15, 2022

(54) METAL OXIDE-BASED CHEMICAL SENSORS

(71) Applicant: VAON, LLC, Bowling Green, KY (US)

(72) Inventors: Vladimir Dobrokhotov, Bowling Green, KY (US); Alexander Larin, Bowling Green, KY (US)

(73) Assignee: VAON, LLC, Bowling Green, KY (US)

( * ) Notice: Subject to any disclaimer, the term of this patent is extended or adjusted under 35 U.S.C. 154(b) by 0 days.

(21) Appl. No.: 17/029,704

(22) Filed: Sep. 23, 2020

(65) Prior Publication Data

US 2021/0010972 A1  Jan. 14, 2021

Related U.S. Application Data

(63) Continuation-in-part of application No. 15/466,712, filed on Mar. 22, 2017, now abandoned.

(60) Provisional application No. 62/361,682, filed on Jul. 13, 2016, provisional application No. 62/312,393, filed on Mar. 23, 2016.

(51) Int. Cl.
*G01N 27/414* (2006.01)
*G01N 33/00* (2006.01)

(52) U.S. Cl.
CPC ..... *G01N 27/4146* (2013.01); *G01N 33/0001* (2013.01); *G01N 33/0031* (2013.01); *G01N 33/0044* (2013.01)

(58) Field of Classification Search
CPC .......... G01N 27/4146; G01N 33/0031; G01N 33/0001; G01N 33/0044; G01N 27/128; G01N 27/127

USPC .......................................................... 422/90
See application file for complete search history.

(56) References Cited

U.S. PATENT DOCUMENTS

| | | |
|---|---|---|
| 4,238,758 A | 12/1980 | Suzuki |
| 4,338,281 A | 7/1982 | Treitinger et al. |
| 4,399,684 A | 8/1983 | Advani et al. |

(Continued)

FOREIGN PATENT DOCUMENTS

WO     86/91992     1/1996

OTHER PUBLICATIONS

Ling, C. et al. (2014). "High hydrogen response of Pd/TiO2/SiO2/Si multilayers at room temperature." Sensors and Actuators B: Chem. 205:255-260. (Year: 2014).*

(Continued)

*Primary Examiner* — Benjamin R Whatley
*Assistant Examiner* — Jacqueline Brazin
(74) *Attorney, Agent, or Firm* — Hollowell Patent Group; Kelly Hollowell

(57) ABSTRACT

Metal oxide-based integrated chemical sensors using a hybrid polycrystalline gas-sensitive material to create a uniform and integrated sensory system. The sensor system provides the unique properties such as improved sensor sensitivity due to reduced thickness, improved selectivity for specific analyte detection in the ppb, faster time of response, decreased time of reset and decreased power consumption in comparison to existing sensor technologies. The present invention also provides novel, metal oxide-based chemical sensor platforms, a novel method of making metal oxide-based chemical sensors, platforms and/or integrated chemical sensors.

7 Claims, 27 Drawing Sheets

(56) References Cited

U.S. PATENT DOCUMENTS

| | | | | |
|---|---|---|---|---|
| 4,453,151 | A | * | 6/1984 | Leary .................... G01N 27/12 338/34 |
| 4,542,640 | A | | 9/1985 | Clifford |
| 4,847,783 | A | | 7/1989 | Grace et al. |
| 5,250,170 | A | | 10/1993 | Yagawara et al. |
| 5,605,612 | A | | 2/1997 | Park et al. |
| 5,783,154 | A | | 7/1998 | Althainz et al. |
| 6,235,243 | B1 | | 5/2001 | Fleischer et al. |
| 7,406,856 | B2 | | 8/2008 | Bottner et al. |
| 2003/0045017 | A1 | | 3/2003 | Hiramatsu et al. |
| 2003/0045019 | A1 | * | 3/2003 | Kubena ............... B81C 1/00904 438/49 |
| 2010/0192687 | A1 | * | 8/2010 | Trakhtenberg ......... G01N 27/12 73/335.02 |
| 2011/0197657 | A1 | * | 8/2011 | Gole .................... G01N 27/127 73/31.05 |
| 2013/0140064 | A1 | | 6/2013 | Burberry et al. |
| 2014/0138259 | A1 | * | 5/2014 | Mickelson ......... G01N 33/0044 205/775 |
| 2018/0017516 | A1 | * | 1/2018 | Dobrokhotov .......... H01L 29/24 |
| 2019/0004020 | A1 | * | 1/2019 | Dobrokhotov ..... G01N 33/0031 |

OTHER PUBLICATIONS

The Karlsruhe Micro Nose, KAMINA, Application Note: 31052, 2008.
Goschnick, J. et al., Condition Monitoring for Intelligent Household Appliances, Sensors in Household Appliances 2002, 5, 52-68.
The Karlsruhe Micronose KAMINA: Novel technology for intelligent systems (brochure).
Arnold, C. et al., Air Quality Monitoring and Fire Detection with Karlsuhe Electronics Micronose Kamina, IEEE Sensor Journal, Aug. 1-22, 2001.
PCT/US2017/023672 International Search Report, published Jun. 9, 2017 (corresponding to PCT application).
PCT/US2017/023672 Written Opinion, published Jun. 9, 2017 (corresponding PCT application).

* cited by examiner

METAL OXIDE-BASED CHEMICAL SENSORS

CROSS REFERENCE TO RELATED APPLICATIONS

This application is a continuation-in-part of U.S. application Ser. No. 15/466,712 filed Mar. 22, 2017, which claims the benefit of both Provisional Application 62/361,682 filed Jul. 13, 2016, and Provisional Application 62/312,393 filed Mar. 23, 2016, the contents of which are all incorporated herein in their entirety by reference thereto.

FIELD OF THE INVENTION

The present invention generally relates to metal oxide-based sensors and platforms and integrated chemical sensors incorporating the same, methods of making the same, and methods of using the same.

BACKGROUND OF THE INVENTION

Chemiresistors (conductometric sensors) are traditionally used as building blocks for integrated chemical sensors (artificial olfactory systems, electronic noses). A chemiresistor is a device whose electrical resistance is modulated by molecular adsorption on its surface. The changes in resistance are proportional to the partial vapor pressure. Hence a chemiresistor converts the concentration of chemicals in the ambient air into a corresponding measurable electrical signal. A chemiresistor is constructed from a vapor-sensitive material placed between conducting leads. One of the best chemically sensitive materials ever discovered is nanoscale tin oxide ($SnO_2$). The sensing mechanism of metal oxides is primarily based on the activation of atmospheric oxygen on the semiconductor surface. Consequently, catalytic reactions of gaseous species with oxygen sites on the surface induce charge transfer from the surface to the bulk, i.e., subsurface, which changes the electrical resistance of the device.

Most conventional chemical sensors are based on recognition of particular analytes, e.g., methane, carbon monoxide, hydrogen sulfide, etc. For complex mixtures, however, this approach is not the most reliable, since it causes frequent false alarms due to cross-sensitivity of sensors to different analytes. The advantage of using integrated sensory systems (electronic noses) is in their ability to learn the chemical signatures of interest, similar to training of canines. Unlike many other analytical techniques, an integrated sensor does not try to separate all the chemical components within a sample, but it perceives a sample as a whole, creating a global fingerprint. For example, the smell that emanates from coffee has hundreds of different chemical components, but our biological olfactory system (and the integrated sensor) simply identifies the total chemical composition as coffee. In an integrated sensor, the headspace from a sample (i.e., the gases emanating from a sample) is delivered to an array of chemical sensors. As each sensor is different in some way (usually broadly tuned to a different chemical group), each sensor's response to a sample is different. These responses can then be used to form a chemical fingerprint of a sample. The response is seen as a change in electrical properties (normally resistance) of the sensor. Specialized software then identifies the sample from this fingerprint.

These sensors usually suffer more or less from cross sensitivity, i.e., apart from their response to a particular target gas they do (to a certain extent) respond to other gases as well. For instance, a methane sensor is also responsive to propane, butane, and natural gas in general. In this respect, a single output sensor cannot be sufficient, even if only one target gas is to be detected. However, a combination of several gas sensors, each providing a different sensitivity spectrum, a so-called sensor array, delivers signal patterns characteristic for the gases to which the array is exposed. These signal patterns enable the distinction between individual gases or gas ensembles. Which gases can or cannot be detected or distinguished depends on the sensor type and the extent of the difference in selectivity between the sensors. Now, the cross sensitivity of the individual sensors, due to a low selectivity even turns out to be an advantage. A low selectivity (in the case of a single sensor a disadvantage for detecting a particular gas), now allows the array to respond to a wide range of gases. A combination of several chemiresistors, each providing a different sensitivity spectrum, a so-called sensor array, delivers signal patterns characteristic for the gases to which the array is exposed.

Overall sensor performance is determined based on a combination of factors such as but not limited to sensitivity, selectivity, stability, time of response and recovery, and power consumption. Sensitivity is defined as a normalized change in conductivity of the sensor element due to the gas (e.g., $H_2S$) exposure. The sensitivity of the sensor can be measured over different ranges of concentrations. Selectivity is determined by the ability of the sensor to respond selectively to a specific analyte or a group analytes. The stability of a sensor is related to its ability to detect an unknown concentration of $H_2S$ after calibration. Time response and recovery is the length of time it takes for a sensor to "reset" after exposure to an analyte and then provide reproducible results with the same sensitivity as previously recorded. Power consumption and temperature distribution relate to the amount of energy required and heat generated during sensor operation. Minimization of power consumption is extremely important for portable sensors.

For more than two decades now, small and simple gas sensors, which provide one output signal only, have been commercially available. Typically, they are manufactured by the sol-gel method, in which metal oxide layers are deposited in the form of a viscous paste and then baked in an inert environment, creating thick films. Metal oxide sensors from Figaro (TGS sensors) and Henan Hanwei Electronics Co., ltd. (MQ sensors) are manufactured by this method. The first integrated sensory systems equipped with arrays assembled from separate sensors were manufactures in the early 90s.

Individually manufactured sensors equipped with sockets are placed in plugs on a carrier plate of several centimeters in size. There are multiple drawbacks associated with this conventional design:

1. The sol-gel process utilized for manufacturing of individual sensors does not provide precise control over the oxide layer thickness. Because of that, variations from sensor to sensor in this manufacturing process are unavoidable. As a consequence, even if the datasheet provides a calibration curve, every sensor manufactured by the sol-gel method requires a calibration and verification by the consumer, using costly specially prepared gaseous mixtures.

2. Individual sensors in a sensor array evolve over time. This phenomenon is known as a long-term drift. For a conventional integrated system, individual elements evolve differently, causing failures of pattern recognition algorithms; requiring ongoing and additional calibrations at a minimum, replacement at maximum.

3. Short-term drift due to the fluctuations in the environment also has different effects on individual elements in a conventional integrated system and causes failures of pattern recognition algorithms.

4. Frequently, individual sensors in a conventional integrated system have variances in response time. This means that some of them respond to analyte exposure faster than the others. Upon exposure to analyte but before reaching a stationary state, sensors of integrated system go through the transient phase. If they are not well-synchronized, during the transient phase, the conventional integrated system typically reports several false results. Synchronization of individual elements of a conventional integrated system is another tune consuming process, and has to be implemented for each unit after the assembly.

5. If one of the sensors in a conventional integrated system fails and needs to be replaced, the entire system will need to undergo synchronization and calibration.

6. The thickness of the metal oxide layer is a key parameter that determines sensor sensitivity. The thinner the layer—the higher the sensitivity. Since only the thick films (sol-gel from 10 to 100 µm (microns) thick) can be produced by the sol-gel method, sensors formed with this method have limited sensitivity. By contrast, the present invention produces a uniform thickness of the metal oxide layer in a range from 10-200 nm (nanometers) thick. For most chemical compounds, the sensitivity of a sol-gel sensor is unable to go below 1 ppm, in contrast to the present invention which produces a sensitivity capable of detecting ppb concentrations.

7. Sol-gel films, which are thick, ranging from 10 to 100 µm (microns) are non-uniform and have a relatively long time of recovery after exposure, which can be up to 1 minute for exposure to high concentrations. By contrast the present invention and sensor only needs 3-4 seconds to recover and respond.

8. Conventional integrated sensory systems are typically large, about 10 cm in size. Discrimination power of an integrated sensor depends on the number of individual basic sensing elements with different chemiresistive properties. However, an increase in the number of sensors inevitably leads to an increase in size, which causes makes a non-uniform distribution of chemicals over the sensor array upon exposure to gaseous analyte.

9. As a consequence of their size, conventional integrated systems often require sophisticated gas sampling systems, splitting the analyte gas into identical fractions for each sensor. Such a sophisticated gas sampling is necessary for simultaneous (synchronized) exposure of all the sensors in the integrated array to the analytes of interest. If the sensors were exposed at different random times (asynchronously), the recognition algorithm would not be able to recognize the chemical patterns. If the integrated sensory system is large, the chemical and physical gradients (variations) across its area are inevitable, so you cannot just put this system in the ambient air and expect all the sensor to be exposed to the same analyte evenly and uniformly at the same time. This is why a sophisticated gas sampling system is necessary for a large conventional integrated system.

10. Conventional integrated sensory systems typically have high power consumption (hundreds of watts). By contrast the present invention has a power consumption of about 250 mW (milliwatts).

11. Conventional integrated sensory systems typically have high manufacturing costs, especially in the case of an advanced sampling system. Synchronization and calibration also make the manufacturing process time-consuming.

In view of the above, it would be advantageous to develop new chemiresistors and integrated chemical sensors and methods of making and using the same, which overcome at least some of the above-noted drawbacks with conventional integrated sensory systems.

SUMMARY OF THE INVENTION

The present invention provides novel, metal oxide-based integrated chemical sensors using a hybrid polycrystalline gas-sensitive material to create a uniform and integrated sensory system. The sensor system provides the unique properties such as improved sensor sensitivity due to reduced thickness, improved selectivity for specific analyte detection in the ppb, faster time of response, decreased time of reset and decreased power consumption in comparison to existing sensor technologies. The present invention also provides novel, metal oxide-based chemical sensor platforms, a novel method of making metal oxide-based chemical sensors, platforms and/or integrated chemical sensors.

These and other aspects, which will become apparent during the following detailed description, have been achieved by the inventors' discovery of new metal oxide-based chemical sensors, metal oxide-based chemical sensor platforms, and metal oxide-based integrated chemical sensors.

BRIEF DESCRIPTION OF THE DRAWINGS

FIG. 4A shows a sensing element before metal oxide deposition. FIG. 4B shows a sensing element after $SnO_2$ (36 nm) deposition. FIG. 4C shows a sensor platform after metal oxide layer deposition.

FIG. 6A shows an integrated sensor platform attached to a package. FIG. 6B shows a platform after the wire bonding. FIG. 6C shows a ball wire bonding geometry.

FIG. 7A shows the modified TO package for an $H_2S$ sensor; FIG. 7B shows the platform and the package with electrical contacts between them; and, FIG. 7C shows a passive $H_2S$ sensor ready for annealing, calibration, and testing.

FIG. 11A shows the selectivity of commercial $H_2S$ sensor MQ136. FIG. 11B shows the selectivity of the present $SnO_2/TiO_2$ sensor.

FIG. 13A shows a platform temperature simulation with cylinder supported structure 1 (ss1). FIG. 13B shows a platform temperature simulation with cone supported structure 2 (ss2). FIG. 13C shows the overall temperature distribution and insulation for TO package design.

FIG. 14A shows a thermal camera image of the sensor's platform (V=3V, I=0.06951A, T=263.85C) with QFI system. FIG. 14B shows the temperature vs. power dissipation for ss1, ss2 and real-life device temperature with QFI thermal camera.

FIG. 15A shows a voltage divider circuit diagram. FIG. 15B shows an electronic circuit board with passive delivery sensor. FIG. 15C shows an electronic circuit board with active delivery system.

FIG. 17A shows a linear projection. The coordinate system is rotated in FIG. 17B in order to minimize the scattering within a single class and maximize inter-class scattering.

FIG. 20A shows a simulated temperature distribution over the microplatform attached to a TO package. FIG. 20B shows optical images of the sensor platform attached to a modified TO package. FIG. 20C shows a single sensing element area. FIG. 20D shows a simulated and experimental temperature distribution across the sensing area under 70 mW heating power. FIG. 20E shows a simulated and experimental data of the sensor average temperature over different power dissipation 8-120 mW.

FIG. 21A shows the schematics of a single-layer sensor. FIG. 21B shows the schematics of a bi-layer sensor. FIG. 21C shows the schematics of a multi-layer sensor.

FIG. 23A show the XRD spectroscopy of samples S0-S3 and S7. FIG. 23B shows the XRD spectroscopy of samples S4-S6. FIG. 23C shows the XRD spectroscopy of a zoom in on the major peaks of the samples S4-S6.

FIG. 24A shows the SEM images of the crystalline structure of $SnO_2$ (S0). FIG. 2BA shows the $SnO_2/TiO_2$ bilayer structure 30 nm+5 nm (S1). FIG. 24C shows the $SnO_2/TiO_2$ bilayer structure 30 nm+10 nm (S2). FIG. 24D shows the $SnO_2/TiO_2$ bilayer structure 30 nm+20 nm (S3). FIG. 24E shows the $SnO_2/TiO_2$ multilayer 5% of $TiO_2$ (S4). FIG. 24F shows the $SnO_2/TiO_2$ multilayer 20% of $TiO_2$ (S5). FIG. 24G shows the $SnO_2/TiO_2$ multilayer 50% of $TiO_2$ (S6). FIG. 24H shows the $TiO_2$ (S7).

FIG. 25A shows the sensors resistance in air under different temperature conditions 100-350 C. FIG. 25B shows the resistance of the sensors in the presence of 10 ppm of $H_2S$ as a function of temperature. FIG. 25C shows the various responses of sensors toward 10 ppm of $H_2S$ over the temperature range.

FIG. 26A shows the sensor response of a S5 multilayer structure (a) to different concentrations of $H_2S$ (from 2 ppm to 20 ppm). FIG. 26B shows the sensor response of an S2 bilayer structure to different concentrations of $H_2S$ (from 2 ppm to 20 ppm). FIG. 26C shows the calibration curves (Response vs. Concentration) for sensors S0-S6.

FIG. 27A shows the response amplitudes of sensors S5 (multilayer structure) and S2 (bilayer structure) to various gases. FIG. 27B shows the response amplitudes sensor S5 to sub-ppm concentrations of $H_2S$ diluted in pure methane.

DETAILED DESCRIPTION OF THE INVENTION

Figure 1:
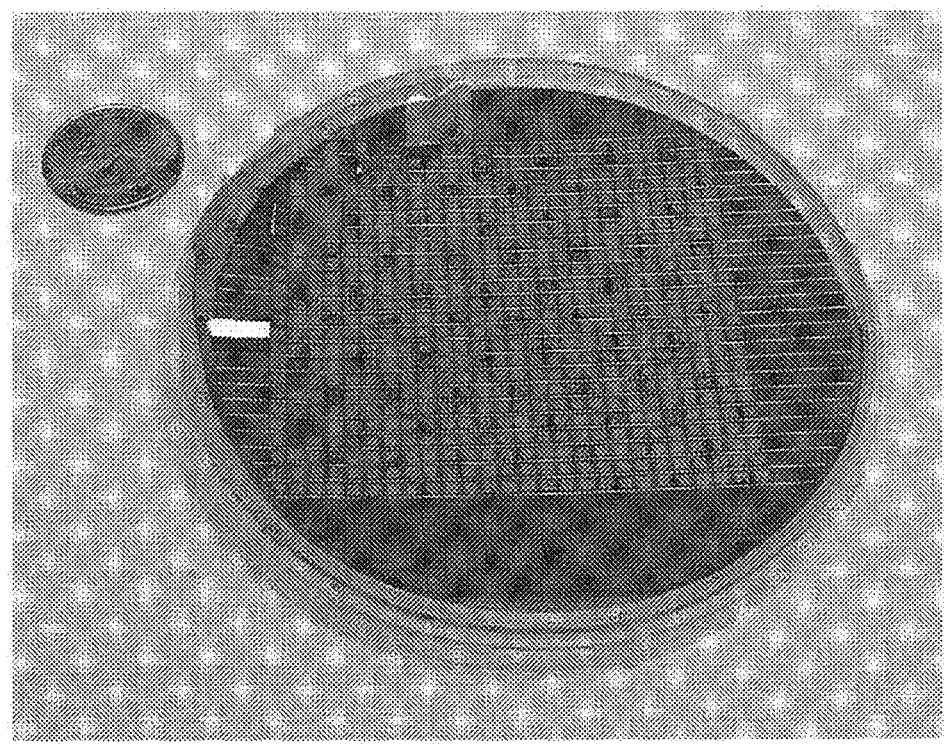
FIG. 1 shows 624 integrated sensors manufactured on 4" silicon wafer in a single manufacturing nm.

In order to overcome the typical limitations of conventional integrated sensory systems, a new highly-integrated multisensory system and manufacturing technique was created. The newly developed manufacturing technique is simple, straight-forward, inexpensive, controllable, and repeatable.

In order to miniaturize the sensor and minimize power consumption, a design was developed that allows one to place multiple sensing elements on a single silicon chip. This "lab-on-a-chip" design utilizes an array of metal leads (e.g., platinum and gold), deposited on a silicon wafer using the stencil (shadow mask) method. Deposition of electrodes is followed by the deposition of catalytic metal oxide layers (islands). Finally, each of the islands is individually treated with different catalytic dopants. The multisensory system is wire-bonded to a multi-pin packaging platform for further integration in an electronic device.

For efficient recognition of analytes, each sensor of the integrated sensory system can be tuned to a certain chemical group (selective); hence each sensor's response to a gaseous species can be different. These responses can then be used to form a chemical fingerprint of an analyte. The discrimination power of the artificial olfactory system comes from the integrated signal from the entire array of sensors. Selectivity of each sensor in the array is defined as the ability to promote only the rate of desired chemical reaction and also retard the undesired reactions.

In one embodiment, the present invention relates to a novel manufacturing technique that allows for tuning the catalytic selectivity of the sensors in the desired manner. This aspect of the invention is based on doping of a metal oxide (e.g., $SnO_2$) with a metallic dopant (e.g., $TiO_2$), using a sputtering technique (or other technique that provides fine control of layer thickness and repeatability). By adsorbing and ionizing molecular oxygen, catalytic metals experience a transition from a metallic state to a metastable quasi-oxidized state, where the oxygen ions are weekly bound to the surfaces of nanoparticles.

A nanoparticle is defined as a particle of matter that is between 1 and 100 nanometers (nm) in diameter. Nanograin is a crystallite of nanoscale size, which is a building block for polycrystalline material. Nanograin is a monocrystalline element (building block) of the polycrystalline structure, connected with the other nanograins through the grain boundaries (heterojunctions and homojunctions). All the nanograins are nanoparticles, but not all the nanoparticles are nanograins. Nanoparticles are a broader class of structures that includes nanograins.

There are several physical and chemical mechanisms that can be attributed to the improvement of the chemiresistor sensitivity and selectivity upon nanoparticles deposition. The mechanisms are described below. The chemical mechanism is the spill-over effect determined by enhanced dissociation of atmospheric oxygen by metal nanoparticles. Better dissociation of oxygen enhances catalytic reactions with chemicals on the surface and amplifies sensor response. The physical mechanism is the enhanced charge transport due to the formation of the nanoscale Schottky contacts at the metal-semiconductor (semiconductor=metal oxide) boundary. These differences are determined by the two primary mechanisms associated with the surface doping of oxides with metal nanoparticles.

The first mechanism is determined by the differences in catalytic activity of nanoscale metals, which is known as the "spillover effect". The presence of dopants (e.g., $TiO_2$ nanoparticles) lowers the electronic work function and decreases the activation energy of the catalytic reaction occurring on the surface of the metal oxide nanograins. The products of catalysis occurring on the metal nanoparticles diffuse onto the metal oxide support (e.g., $SnO_2$), which acts as a reagent delivery system for the metal nanoparticle, amplifying the chemical processes occurring at the metal oxide surface (e.g., $SnO_2$), and dramatically modifying the oxide electronic behavior. The binding energy of the ionized oxygen species in the steady state, the catalytic reaction rate upon exposure to a vapor pulse, and the charge transfer rate from the surface to the bulk of the metal oxide (e.g., $SnO_2$) is strongly dependent on the electronic work function of the nanoparticles (e.g., $TiO_2$) and metal oxide support (e.g., $SnO_2$). Hence, the same analyte will generate different conductivity changes in chemiresistors functionalized with different nanoparticles (e.g., $TiO_2$ vs. Pt).

The second mechanism has a primarily physical nature, but also strongly depends on the work function of the vapor-sensitive materials. The deposition of nanoparticles (e.g., $TiO_2$ nanoparticles) on the semiconductor layer (e.g., $SnO_2$ nanograins) leads to the formation of a large amount of nanoscale metal-semiconductor Schottky contacts (Schottky barriers) over the metal oxide layer. The energy barrier height of the Schottky contacts is determined by the difference between the work functions W of the metal and the semiconductor $\Delta E = W_m - W_s$. For example, the coating of $SnO_2$ with catalytic nanoparticles such as Pt (W=5.12-5.93 eV), Pd (W=5.22-5.6 eV), Au (W=5.1-5.47 eV), Ni (W=5.04-5.35 eV), and Cu (W=4.53-5.1 eV) leads to a formation of Schottky contacts with different barrier heights.

In the $SnO_2$-nanoparticle chemiresistor, the external electrostatic potential is induced on nanoparticles by the adsorbed oxygen species. Exposure of the chemiresistor to a vapor pulse temporarily removes the adsorbed oxygen and causes a drop in the electrostatic potential induced on nanoparticle causing charge transfer from the nanoparticle to the semiconductor support. This mechanism of current modulation is similar to the field effect transistor, where the nanoparticle acts as a gate and the adsorbed oxygen molecules work as a source of electrostatic potential. Since the depletion depth and the amount of transferred charge are both determined by the value of $\Delta E$, the physical discrimination mechanism is also determined by the work functions of the nanoparticles and $SnO_2$ support.

In the present invention, the catalytic reaction activation energy is timed in a desired manner. It now has been found that certain surface modifications make catalytic properties of sensors highly-preferential toward a particular analyte. In this way, the surface is able to trigger only the reactions with particular activation energy. The sensors of the present invention can be separated into five groups as described below.

1. Sensors of gases acidic in nature: these sensors are $SnO_2$-based and tuned toward acidic sensitivity by surface doping with Cu nanoparticles forming basic oxide CuO. The basic nature of CuO makes the interactive layer very selective to acidic gases like $H_2S$ and mercaptans.

2. Sensors of gases basic in nature: these sensors are $SnO_2$-based and tuned toward basic sensitivity by surface doping with Mo nanoparticles forming acidic oxide $MoO_3$. These sensors have preferential sensitivity towards $NH_3$ and amines.

3. Sensors of oxidizing gases (e.g., $O_2$ and $NO_2$): these sensors are $SnO_2$-based and tuned toward oxidizing sensitivity by surface doping with Ni nanoparticles forming oxide NiO.

4. Sensors of reducing gases without well-pronounced acidic/basic properties (e.g., CO, $H_2$, and $CH_4$): these sensors are $SnO_2$-based and tuned toward reducing gases by surface doping with nanoparticles of noble metals forming quasi-stable clusters, e.g., $Pd_nO_m$ and $Pt_nO_m$.

5. Sensors of organic vapors (e.g., ethanol, benzene, toluene, ethylbenzene, xylene etc.): These sensors are $SnO_2$-based and tuned toward acidic sensitivity by doping with Fe nanoparticles forming basic oxide $Fe_2O_3$.

Deposition of Gas-Sensitive Layers:

In an aspect of the present invention the metal oxide and dopant layers are applied by sputtering. Conventional sensors are prepared by the standard sol-gel technique, which is based on deposition of small droplets of metal oxide paste. The present sputtering technique is superior to sol-gel method for the following reasons.

The first major drawback of sol-gel method is the large layer non-uniform thickness from 10 to 100 μm (microns), and hence limited sensitivity. Second, the deposition of microdroplets does not provide a complete control over the layer geometry and thickness. As a consequence of that, variations from sensor to sensor in this manufacturing process are unavoidable. Third, sensor response and recovery time for thick films is much longer than the thin films obtainable with sputtering, especially for large concentrations of analytes (gases). Because of the lack of control over sol-gel deposition, sensor voltage output cannot be predicted. Therefore, each sensor requires independent calibration using special gas mixes, which adds manufacturing cost and time. Oxide powder, used for paste preparation in sol-gel method, consists of micrograins, obtained by milling of bulk metal oxide. This technology is also known as top-down approach. Multiple studies indicate that microstructures obtained by top-down approach have relatively low chemical reactivity and sensitivity and cannot produce a uniform grain size or a thin uniform layer of material, compared to self-assembled nanograins, obtained by bottom-up approach (e.g., sputtering) which does produce a uniform grain size and uniform thickness of the layer deposited with a thickness in the range of 10-200 nm.

In contrast to the sol-gel method, the present sputtering method creates an ultra-thin layer of a precisely controlled geometrical shape. This provides: ultra-high sensitivity, ultra-fast response and recovery time, and elimination of variations from sensor to sensor. Sensor behavior becomes predicable, because the manufacturing process is fully controllable. Sensors formed this way can be implemented immediately and independent calibration of every device is no longer necessary for relatively high concentrations (50 ppm and higher). Of course, for ultra-precise sub-ppm measurements, calibration is still useful. Finally, the present manufacturing technique is based on self-assembly of metal-oxide nanograins and functionalization with metal nanoparticles, also known as a bottom-up approach.

Integrated System Design, Manufacturing and Maintenance:

The present manufacturing technique allows for fast manufacturing of large quantities of sensors. FIG. 1 demonstrates the simultaneous manufacturing of 624 chemical sensor platforms on a single wafer. For conventional sol-gel systems it would be equivalent to precise targeting and deposition of 2496 droplets, which is extremely expensive and time consuming.

Conventional integrated sensory systems are typically large in size. Discrimination power of an integrated sensor depends on the number of individual basic sensing elements with different catalytic properties. However, an increase in the number of sensors inevitably leads to an increase in size, which causes a non-uniform distribution of chemicals over the sensor array upon exposure to gaseous analyte leading to false recognition. In contrast to a conventional system, the disclosed highly-integrated system provides a physical placement of all the sensors at the same point (or nearly) in space. This design assures a uniform exposure of all the sensors to chemicals and, hence, an accurate recognition and concentration measurements.

Because of the large size, conventional integrated systems require sophisticated gas sampling systems, splitting the analyte gas into identical fractions for each sensor. Conventional integrated sensory systems typically have high manufacturing costs, especially in case of an advanced sampling system. Synchronization and calibration make the manufacturing process time-consuming. Conventional integrated sensory systems typically have high power consumption (hundreds of watts). In contrast, the disclosed integrated system performs accurately even with a very primitive sampling system, can consume about tens of mV of power and has a manufacturing cost lower than that for a simple single-gas conventional sensor.

Operational Characteristics of Integrated Systems:

Individual sensors in the array evolve over time. This phenomenon is known as a long-term drift. For a conventional integrated system, individual elements evolve differently, causing failures of pattern recognition algorithms. Short-term drift due to the fluctuations in the environment also has different effect on individual elements and also causes instabilities in pattern recognition algorithms.

Frequently, individual sensors of a conventional integrated system have variances in time constant, response, and recovery time. This means that some of them respond to exposures faster than the others. Upon exposure to analyte, before reaching the stationary state, sensors of an integrated system go through a transient phase. If they are not well-synchronized, during the transient phase, the integrated system typically reports several false results. Synchronization of individual elements of a conventional integrated system is another time consuming process, and has to be implemented for each unit after the assembly.

An advantage of the present invention is that all the elements of the highly integrated array have the same dynamics for the long-term and short-term drift. Also, the time constant, response and recovery time is the same for all of them, meaning that the sensors are perfectly synchronized. Thanks to that the robust recognition is preserved even during the transient response.

In an aspect, the present invention provides a novel chemical sensor, comprising: (a) an oxidized silicon wafer, comprising: a silicon layer sandwiched between a top ($1^{st}$) silicon oxide ($SiO_2$) layer and a bottom ($2^{nd}$) $SiO_2$ layer, the top $SiO_2$ layer, comprising: a sensor area; (b) a heating element in contact with the $1^{st}$ $SiO_2$ layer and located near at least one edge of the sensor area; (c) a pair of electrical leads in contact with the Pt $SiO_2$ layer and at least partly located on the sensor area; (d) a metal oxide layer located on the sensor area and in contact with at least a part of the pair of electrical leads and the $1^{st}$ $SiO_2$ layer; and, (e) a dopant layer in contact with the metal oxide layer.

In an aspect, the present invention provides a novel chemical sensor, comprising: (a) an oxidized silicon membrane, comprising a silicon (Si) layer and a silicon oxide ($SiO_2$) layer, wherein the $SiO_2$ layer is located on top of the silicon layer and, comprises: a sensor area; (b) a heating element in contact with the $SiO_2$ layer and located near at least one edge of the sensor area; (c) a pair of electrical leads in contact with the $SiO_2$ layer and at least partly located on the sensor area; (d) a metal oxide layer located on the sensor area and in contact with at least a part of the pair of electrical leads and the $SiO_2$ layer; and, (e) a dopant layer in contact with the metal oxide layer.

Membrane (sometimes referred to as a "floating" sensor) refers to a $SiO_2$/Si wafer that is typically formed from an oxidized silicon wafer (e.g., a wafer having $SiO_2$/Si/$SiO_2$ layers). The membrane is formed by removing one of the $SiO_2$ layers (e.g., the bottom layer) and a substantial portion of the Si layer. Typically part of the original wafer ($SiO_2$/Si/$SiO_2$) is left to serve as connectors for the membrane (e.g., leaving the 4 corner pieces of the original wafer as the "connectors" to the membrane).

In another aspect, the present invention provides a novel chemical sensor platform, comprising: (a) an oxidized silicon wafer, comprising: a silicon layer sandwiched between a top ($1^{st}$) silicon oxide ($SiO_2$) layer and a bottom ($2^{nd}$) $SiO_2$ layer, the $1^{st}$ $SiO_2$ layer, comprising: a plurality of separate sensor areas; (b) at least one heating element in contact with the $1^{st}$ $SiO_2$ layer and located near at least one edge of a sensor area; (c) a plurality of electrical leads, each in contact with the $1^{st}$ $SiO_2$ layer, wherein 1 pair of electrical leads is at least partly located on each of the separate sensor areas; (d) a plurality of metal oxide layers, wherein 1 metal oxide layer is located on each of the plurality of sensor areas and in contact with at least a part of the pair of electrical leads located on the same area; and, (e) a plurality of dopant layers, wherein 1 dopant layer is located on each of the plurality of sensor areas and in contact with the metal oxide layer in the same area.

In another aspect, the present invention provides a novel chemical sensor platform, comprising: (a) an oxidized silicon membrane, comprising a silicon (Si) layer and a silicon oxide ($SiO_2$) layer, wherein the $SiO_2$ layer is located on top of the silicon layer and, comprises: a plurality of separate sensor areas; (b) at least one heating element in contact with the $SiO_2$ layer and located near at least one edge of each sensor area; (c) a plurality of pairs of electrical leads, each in contact with the $SiO_2$ layer, wherein 1 pair of electrical leads is at least partly located on each of the separate sensor areas; (d) a plurality of metal oxide layers, wherein 1 metal oxide layer is located on each of the plurality of sensor areas and is in contact with at least a part of the pair of electrical leads located on the same area; and, (e) a plurality of dopant layers, wherein 1 dopant layer is located on each of the plurality of sensor areas and in contact with the metal oxide layer in the same area.

The number of sensor areas in the chemical sensor platform varies. Examples include 2, 3, 4, 5, 6, 7, 8, 9, 10, or more. The number of sensor areas determines the number of pairs of electrical leads, metal oxide layers, and dopant layers. The number of heating elements is independent of the number of sensor areas. One heating element can service more than one sensor area. Examples of the number of heating elements includes 1, 2, 3, 4, 5, or more.

In another aspect, the plurality is 4. In another aspect, the number of sensor areas is 4. In another aspect, in the chemical sensor platform there are 4 separate sensor areas, 1 heating element, 4 pairs of electrical leads, 4 metal oxide layers, and 4 dopant layers. In another aspect, in the chemical sensor platform there are 4 separate sensor areas, 1 Pt heating element, 4 pairs of Pt electrical leads, 4 $SnO_2$ (metal oxide) layers, and 4 dopant layers.

In another aspect, in the chemical sensor platform there are 4 separate sensor areas, 1 Pt heating element, 4 pairs of Pt electrical leads, 4 $SnO_2$ (metal oxide) layers, 4 dopant layers, and 4 $Si/SiO_2$ connectors. In another aspect, in the chemical sensor platform there are 4 separate sensor areas, 1 Pt heating element, 4 pairs of Pt electrical leads, 4 $SnO_2$ (metal oxide) layers, 4 dopant layers, and 4 $SiO_2/Si/SiO_2$ connectors. In another aspect, in the chemical sensor platform there are 4 separate sensor areas, 1 Pt/Ti (Ti being the $2^{nd}$ material) heating element, 4 pairs of Pt/Ti (Ti being the $2^{nd}$ material) electrical leads, 4 $SnO_2$ (metal oxide) layers, and 4 dopant layers.

In another aspect, in the chemical sensor platform there are 4 separate sensor areas, 1 Pt/Ti (Ti being the $2^{nd}$ material) heating element, 4 pairs of Pt/Ti (Ti being the $2^{nd}$ material) electrical leads, 4 $SnO_2$ (metal oxide) layers, 4 dopant layers, and 4 $Si/SiO_2$ connectors.

In another aspect, in the chemical sensor platform there are 4 separate sensor areas, 1 Pt/Ti (Ti being the $2^{nd}$ material) heating element, 4 pairs of Pt/Ti (Ti being the $2^{nd}$ material) electrical leads, 4 $SnO_2$ (metal oxide) layers, 4 dopant layers, and 4 $SiO_2/Si/SiO_2$ connectors.

Nanocrystals are the building blocks of nanograins/nanoparticles. Nanograin is a crystallite of nanoscale size, which is a building block for polycrystalline material. Nanograin is a monocrystalline element (building block) of the polycrystalline structure, connected with the other nanograins through the grain boundaries (heterojunctions and homojunctions). Nanoparticle is defined as a particle of matter that is between 1 and 100 nanometers (nm) in diameter. All the nanograins are nanoparticles, but not all the nanoparticles are nanograins. Nanoparticles are a broader class of structures that includes nanograins. Nanocrystals agglomerate into nanograins/nanoparticles (metal oxide/dopant)(nanograins being larger than nanoparticles). The size of nanograins/nanoparticles vary in a range from about 5, 10, 15, 20, 25, 30, 35, 40, 45, 50, 55, 60, 65, 70, 75, 80, 85, 90, 95, to about 100 nm, depending on the type of material and its ability to agglomerate into bigger particles.

The description herein applies to both sensors and platforms, where ever appropriate.

In the chemical sensor (or platform), the $1^{st}$ $SiO_2$ layer is typically polished. The sensor area is where at least part of a pair of electrical leads is located as well as the metal oxide and dopant layers. The heating element is not in contact with the electrical leads, the metal oxide layer, or the dopant layer but is located close enough to be able to heat the metal oxide and dopant layers. The dopant layer substantially if not entirely covers the exposed or top side of the metal oxide layer.

In another aspect, the oxidized silicon wafer is about 100, 150, 200, 250, 300, 350, 400, 450, to 500 µm thick. In another aspect, the oxidized silicon wafer is about 200 µm thick.

In another aspect, the part of the $2^{nd}$ $SiO_2$ layer located beneath the plurality of sensor areas (or sensor area, if only 1 is present) is absent and a substantial portion of the corresponding silicon layer is absent. In this aspect, part of the bottom of the wafer is absent, including all of the $2^{nd}$ $SiO_2$ layer and some of the bottom of the silicon layer.

In another aspect, the corresponding part of the silicon layer located beneath the plurality of sensor areas (or sensor area, if only 1 is present) is about 5, 10, 15, 20, 25, 30, 35, 40, 45, 50, 55, 60, 65, 70, 75, 80, 85, 90, 95, to 100 µm thick. This is measured from the bottom of the $1^{st}$ $SiO_2$ layer to the bottom of the wafer (no $2^{nd}$ $SiO_2$ layer is present on this part of the silicon layer). In another aspect, the corresponding part of the silicon layer located beneath plurality of sensor areas (or sensor area, if only 1 is present) is about 50 µm thick.

In another aspect, part of the $1^{st}$ $SiO_2$ layer at the edges of the plurality of sensor areas (or sensor area, if only 1 is present) is absent, thereby forming a discontinuous trench around the plurality of sensor areas (or sensor area, if only 1 is present). The $1^{st}$ $SiO_2$ layer that is in contact with the electrical leads remains. The absence of the $1^{st}$ $SiO_2$ layer at the edges of the sensor area, but not including the $1^{st}$ $SiO_2$ layer that is in contact with the electrical leads, creates a trench that partially isolates the $1^{st}$ $SiO_2$ layer in the sensor area from the $1^{st}$ $SiO_2$ layer outside of the sensor area. This trench can be deepened by removal of the silicon at the bottom of the trench. Finally, when the $2^{nd}$ $SiO_2$ under the sensor area is removed and part of the corresponding part of the silicon layer is removed, the trench becomes an actual opening. The remaining $1^{st}$ $SiO_2$ layer in the sensor area and the corresponding silicon layer underneath are then "floating". The floating area is called a membrane.

In another aspect, part of the $1^{st}$ $SiO_2$ layer at the edges of the plurality of sensor areas (or sensor area, if only 1 is present) and part of the corresponding silicon layer is absent, thereby forming a discontinuous trench around the plurality of sensor areas (or sensor area, if only 1 is present).

In another aspect, in the chemical platform (or chemical sensor): the part of the $2^{nd}$ $SiO_2$ layer located beneath the plurality of sensor areas (or sensor area, if only 1 is present) is absent and a substantial portion of the corresponding part of silicon layer is absent; and, the part of the $1^{st}$ $SiO_2$ layer at the edges of the plurality of sensor areas (or sensor area, if only 1 is present) and the silicon layer directly beneath is absent, thereby forming a discontinuous opening around the plurality of sensor areas (or sensor area, if only 1 is present).

In another aspect, the corresponding part of the silicon layer is about 5, 10, 15, 20, 25, 30, 35, 40, 45, 50, 55, 60, 65, 70, 75, 80, 85, 90, 95, to 100 µm thick. This is measured from the bottom of the $1^{st}$ $SiO_2$ layer to the bottom of the wafer (no $2^{nd}$ $SiO_2$ layer is present on this part of the silicon layer). In another example, the corresponding part of the silicon layer is about 50 µm thick.

In another aspect, the metal oxide of the plurality of metal oxide layers is the same. In another aspect, the metal oxide of the plurality of metal oxide layers is different. In another aspect, the metal oxide layers are the same thickness. In another aspect, all of the metal oxide layers are of different thicknesses.

In another aspect, the dopant of the plurality of dopant layers is the same. In another aspect, the dopant of the plurality of dopant layers is different. In another aspect, all dopant layers are the same thickness. In another aspect, all of the dopant layers are of different thicknesses.

In another aspect, the $1^{st}$ and $2^{nd}$ $SiO_2$ layers (in the sensor or platform) are independently about 200 to 400 nm thick. In another aspect, the $1^{st}$ and $2^{nd}$ $SiO_2$ layers are independently about 300 nm thick.

In another aspect, the at least one heating element (or heating element for the chemical sensor), independently comprises: a $1^{st}$ material selected from Pt, Au, and polysilicon. In another aspect, the at least one heating element, comprises: Pt.

In another aspect, the heating element is about 50, 100, 150, 200, 250, 300, 350, 400, 450, 500, 550, 600, 650, 700, 750, 800, 850, 900, 950 to 1,000 nm thick. In another aspect, the heating element is about 300 nm thick.

In another aspect, the heating element, further comprises: a $2^{nd}$ material layer sandwiched between the $1^{st}$ $SiO_2$ layer and the $1^{st}$ material layer. In another aspect, the $2^{nd}$ material layer, comprises: a metal selected from Ti and Cr. In another aspect, the $2^{nd}$ material layer, comprises: Ti. In another aspect, the $2^{nd}$ material layer is about 1, 2, 3, 4, 5, 6, 7, 8, 9, to 10 nm thick. In another aspect, the $2^{nd}$ material layer is about 2 nm thick. In another aspect, the $2^{nd}$ material layer is about 5 nm thick.

In another aspect, the plurality of electrical leads (or electrical lead in the chemical sensor), comprise: a $1^{st}$ metal layer independently selected from Pt and Au. In another aspect, the plurality of electrical leads, comprise: Pt. In another aspect, the plurality of electrical leads are about 50, 100, 150, 200, 250, 300, 350, 400, 450, 500, 550, 600, 650, 700, 750, 800, 850, 900, 950 to 1,000 nm thick. In another aspect, the plurality of electrical leads (or lead in the chemical sensor) are about 300 nm thick.

In another aspect, the plurality of electrical leads (or electrical lead in the chemical sensor), each further comprise: a $2^{nd}$ metal, layer sandwiched between the $1^{st}$ $SiO_2$ layer and the $1^{st}$ metal layer. In another aspect, each $2^{nd}$ metal layer, comprises: a metal independently selected from Ti and Cr. In another aspect, each $2^{nd}$ metal layer, comprises: Ti. In another aspect, each $2^{nd}$ metal layer is independently about 1, 2, 3, 4, 5, 6, 7, 8, 9, to 10 nm thick. In another aspect, each $2^{nd}$ metal layer is independently about 2 nm thick. In another aspect, each $2^{nd}$ metal layer is independently about 5 nm thick.

In another aspect, the metal oxide layer or plurality of metal oxide layers is deposited via sputtering. In another aspect, the dopant layer or the plurality of dopant layers is deposited via sputtering. In another aspect, each metal oxide is independently selected from: $SnO_2$, $ZnO$, $V_2O_5$, $WO_3$, $TiO_2$, $Al_2O_3$, and $Fe_2O_3$. In another aspect, each metal oxide is $SnO_2$. In another aspect, each metal oxide layer is independently about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, to 40 nm thick.

The dopant layer being in contact with the metal oxide layer "dopes" the metal oxide layer. Dopes or dopant refers to the surface modification of the metal oxide layer (e.g., $SnO_2$) by the dopant layer. In another aspect, each dopant is independently selected from: Ti, $TiO_2$, Au, Cu, CuO, $Cu_2O$, Mo, $MoO_2$, $MoO_3$, Ni, NiO, $Ni_2O_3$, Pt, Pd, Ag, AgO, Ru, $RuO_2$, Rh, $Rh_2O_3$, Os, $OsO_2$, $OsO_4$, Ir, and $IrO_2$. In another aspect, the dopant is $TiO_2$.

In another aspect, each dopant layer is independently about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, to 15 nm thick.

In another aspect, the portions (or portion for the chemical sensor) of the $2^{nd}$ $SiO_2$ layer under the corresponding plurality of sensor areas (or area for the chemical sensor) is absent and the thickness of the plurality of sensor areas (or area), as measured from the top of the corresponding dopant layers to the bottom of the corresponding silicon layers (or layer)(i.e., the thickness of the plurality of sensor membranes (or sensor membrane)), is from 50, 100, 150, 200, 250, 300, 350, 400, 450 to 500 µm. In another aspect, the thickness of the plurality of membranes (or membrane) is 200 µm. In another aspect, the thickness of the plurality of membranes (or membrane) is 100 µm. In another aspect, the thickness of the plurality of membranes (or membrane) is 50 µm.

In another aspect, the present invention provides a novel method of forming a chemical sensor platform, comprising:

(a) depositing at least one heating element and a plurality of pairs of electrical leads (e.g., 4 pairs) onto an oxidized silicon wafer, wherein: (i) the oxidized silicon wafer, comprises: a silicon layer sandwiched between a top ($1^{st}$) silicon oxide ($SiO_2$) layer and a bottom ($2^{nd}$) $SiO_2$ layer; (ii) the $1^{st}$ $SiO_2$ layer, comprises: a plurality of separate sensor areas (e.g., 4); (iii) the at least one heating element and plurality of pairs of electrical leads are deposited onto the $1^{st}$ $SiO_2$ layer; (iv) the at least one heating element is located near at least one edge of at least one sensor area; and, (v)1 pair of electrical leads is at least partly located on each of the separate sensor areas (e.g., 4 pairs); (b) depositing a metal oxide layer onto each of the plurality of sensor areas and the 1 pair of electrical leads located thereon; (c) depositing a dopant layer over each of the plurality of metal oxide layers (e.g., 4 metal oxide layers); and, (d) annealing the resulting platform at a sufficient temperature and for a sufficient time to cause at least a portion of each metal oxide layer (e.g., 4 metal oxide layers) to form nanograins and at least a portion of each dopant layer (e.g., 4 dopant layers) to form nanoparticles.

In the method, each metal oxide layer is in contact with at least a part of 1 pair of electrical leads and part of the sensor area not covered by the electrical leads. It is noted that neither the electrical leads nor the metal oxide layer is typically in contact with the heater. The dopant layer is substantially the same dimensions as the metal oxide layer and substantially covers the top side of the metal oxide layer.

In another aspect, the method, further comprises: (e) etching away part of the $1^{st}$ $SiO_2$ layer at the edges of the plurality of sensor areas and part of the corresponding silicon layer to form a discontinuous trench around the plurality of sensor areas.

In another aspect, the method, further comprises: (f) etching away the part of the $2^{nd}$ $SiO_2$ layer located beneath the plurality of sensor areas and part of the corresponding silicon layer, wherein enough of the silicon layer is removed to convert the discontinuous trench into a discontinuous opening in the silicon wafer.

In another aspect, plurality is 4.

In another aspect, etching (f) is completed prior to annealing (e).

In another aspect, the method, further comprises: (i) prior to depositing (e), applying a $1^{st}$ photomask to the $1^{st}$ $SiO_2$ layer; and, (h) after depositing (a), removing the $1^{st}$ photomask.

In another aspect, the method, further comprises: (i) prior to etching (e), applying a $2^{nd}$ photomask to the $1^{st}$ $SiO_2$ layer; and, (j) after etching (e), removing the $2^{nd}$ photomask.

In another aspect, the method, further comprises: (k) prior to depositing (b), applying a $3^{rd}$ photomask to the $1^{st}$ $SiO_2$ layer; and, (l) after depositing (c), removing the $3^{rd}$ photomask.

In another aspect, the method, further comprises: (m) prior to etching (f), applying a $4^{th}$ photomask to the $2^{nd}$ $SiO_2$ layer; and, (n) after etching (f), removing the $4^{th}$ photomask.

In another aspect, the method, further comprises: (o) prior to depositing (a), depositing an adhesive metal layer. The adhesive metal layer is the $2^{nd}$ material layer sandwiched between the $1^{st}$ $SiO_2$ layer and the $1^{st}$ material layer.

A multilayer structure or sensing layer is a thin film is obtained by multiple consecutive depositions of a metal oxide and a dopant (e.g., $SnO_2$, then $TiO_2$, then $SiO_2$, then $TiO_2$, etc.).

In another aspect, the present invention provides a novel multilayer chemical sensor, comprising: (a) an oxidized silicon wafer, comprising: a silicon layer sandwiched between a top (1st) silicon oxide (SiO$_2$) layer and a bottom (2nd) SiO$_2$ layer, the top SiO$_2$ layer, comprising: a sensor area; (b) a heating element in contact with the 1st SiO$_2$ layer and located near at least one edge of the sensor area; (c) a pair of electrical leads in contact with the 1st SiO$_2$ layer and at least partly located on the sensor area; (d) a sensing layer, comprising: alternating layers of metal oxide and dopant, wherein the sensing layer is located on the sensor area and the first metal oxide layer is in contact with at least a part of the pair of electrical leads and the 1st SiO$_2$ layer.

In another aspect, the sensing layer, comprises: from 4, 5, 6, 7, 8, 9, 10, 11, 12, 13, 14, 15, 16, 17, 18, 19, to 20 layers (though typically there are an even number of layers with the dopant being the outermost layer). In another aspect, the sensing layer, comprises: 6 layers.

In another aspect, from 5-50% by volume of the sensing layer is the dopant. In another aspect, 5% by volume of the sensing layer is the dopant. In another aspect, 10% by volume of the sensing layer is the dopant. In another aspect, 15% by volume of the sensing layer is the dopant. In another aspect, 20% by volume of the sensing layer is the dopant.

In another aspect, the present invention provides a novel method of forming a chemical sensor platform, comprising: (a) depositing at least one heating element and a plurality of pairs of electrical leads onto an oxidized silicon wafer, wherein: (i) the oxidized silicon wafer, comprises: a silicon layer sandwiched between a top (1st) silicon oxide (SiO$_2$) layer and a bottom (2nd) SiO$_2$ layer; (ii) the 1st SiO$_2$ layer, comprises: a plurality of separate sensor areas; (iii) the at least one heating element and plurality of pairs of electrical leads are deposited onto the 1st SiO$_2$ layer; (iv) the at least one heating element is located near at least one edge of at least one sensor area; and, (v) 1 pair of electrical leads is at least partly located on each of the separate sensor areas; (b) depositing a plurality of sensing layers, each sensing layer, comprising: alternating layers of metal oxide and dopant, wherein 1 sensing layer is located on each sensor area and each first metal oxide layer is in contact with at least a part of the pair of electrical leads and the 1st SiO$_2$ layer; and, (c) annealing the resulting platform at a sufficient temperature and for a sufficient time to cause at least a portion of each metal oxide layer to form nanograins and at least a portion of each dopant layer to form nanoparticles.

In another aspect, the method, further comprises: (d) etching away part of the 1st SiO$_2$ layer at the edges of the plurality of sensor areas and part of the corresponding silicon layer to form a discontinuous trench around the plurality of sensor areas.

In another aspect, the method, further comprises: (e) etching away the part of the 2nd SiO$_2$ layer located beneath the plurality of sensor areas and part of the corresponding silicon layer, wherein enough of the silicon layer is removed to convert the discontinuous trench into a discontinuous opening in the silicon wafer.

In another aspect, the plurality is 4.

In another aspect, the etching (e) is completed prior to annealing (c).

In another aspect, the method, further comprises: (f) prior to depositing (a), applying a 1st photomask to the 1st SiO$_2$ layer; and, (g) after depositing (a), removing the 1st photomask.

In another aspect, the method, further comprises: (h) prior to etching (d), applying a 2nd photomask to the 1st SiO$_2$ layer; and, (i) after etching (d), removing the 2nd photomask.

In another aspect, the method, further comprises: (j) prior to depositing (b), applying a 3rd photomask to the 1st SiO$_2$ layer; and, (k) after depositing (b), removing the 3rd photomask.

In another aspect, the method, further comprises: (l) prior to etching (e), applying a 4th photomask to the 2nd SiO$_2$ layer; and, (m) after etching (e), removing the 4th photomask.

In another aspect, the method, further comprises: (n) prior to depositing (a), depositing an adhesive metal layer.

In another aspect, the present invention provides a novel, integrated chemical sensor that can be used in the following applications. (a) Sensor components for confined space gas monitors, leak detectors and analytical instruments. The present sensor can replace traditional metal oxide sensors in their standard applications for gas detection. The application determines the type of sampling system (active or passive). (b) Alcohol monitors inside vehicles for prevention of drunk driving. (c) Sensors utilized in cooking processes for prevention of overcooking and burning. (d) Built-in sensors for cell phones and microphones. (e) Built-in sensors for food freshness and safety monitoring for refrigerators.

The following examples are meant to illustrate, not limit, the present invention.

EXAMPLE 1

A general description of the novel manufacturing process for making sensors and the highly-integrated sensors of the present invention is as follows:

Starting Substrate:

An oxidized silicon wafer is used as the substrate for the sensors and platforms of the present invention. A platform of the present invention is a unit that comprises multiple sensors and pairs of electrical leads and at least one heating element. The present manufacturing process allows for numerous platforms to be formed simultaneously on one oxidized silicon wafer. As will be described below, each platform may contain only one type of sensor (e.g., all sensors have the same metal oxide/dopant layers) or each sensor on the platform may have a variety of different sensor types (e.g., 2, 3, 4, or more).

A typical wafer is 4" in diameter, but a larger wafer (e.g., 6" in diameter) can be used in order to increase the number of devices per manufacturing cycle and decrease the manufacturing cost per device. The orientation of the wafer can be 100. One side (the "top" side) of the wafer is typically polished. An example of the thickness of the wafer is 200 μm. Other examples of the thickness of the wafer include from about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, to 500 μm thick. The thinner the wafer (e.g., 200 μm, 150 μm, or 100 μm), the lower the power consumption of the resulting device.

A 1st layer of oxidized silicon (SiO$_2$) is present on the top of the wafer. A 2nd layer of oxidized silicon (SiO$_2$) is present on the bottom of the wafer. Since the wafer is polished, it is the layer of SiO$_2$ that is polished. An example of the thickness of the oxide layers is about 300 nm. Other examples of the thickness of the SiO$_2$ layers include from about 200, 210, 220, 230, 240, 250, 260, 270, 280, 290, 300, 310, 320, 330, 340, 350, 360, 370, 380, 390 to 400 nm thick.

Applying Photomask #1:

Each sensor has to be thermally activated in order to act as a conductometric sensor. Thus, a microheater (heating element) has to be deposited for each sensor or on each platform. Also, interdigitated metal terminals (electrical leads) have to be deposited for monitoring of signals from each of the sensor areas (change in conductance caused by a chemical reaction). Patterns for both the microheater and terminals, for the numerous platforms that can be simultaneously made, can be deposited on the wafer using photolithography, as follows.

A photoresist (Photomask #1) is spin coated on the front side (i.e., polished side) of the wafer. The photoresist is chosen based on its desired thickness (thick enough to allow for deposition of the heater and metal leads, but not too thick to make it difficult to use). For example, photoresist 1827, a positive photoresist that is expected to produce a 2.7 µm layer @ 4000 rpm spin, can be used. It is applied by spinning the wafer for 0.2 sec @ 500 rpm while the photoresist is applied, and then for 10 sec @ 4000 rpm. Other examples of the thickness of the photoresist to be applied include from about 2, 3, 4, 5, 6, 7, 8, 9, to 10 µm.

After spin coating, the wafer is "soft baked" by heating at (e.g., 90° C. in air for about 70-75 sec). The "soft baked" wafer is then exposed to UV light appropriate for the photoresist (e.g., 325W for about 22 seconds), followed by a toluene bath (60 sec), blow drying with $N_2$, and another soft baking (e.g., 90° C. in air for about 15 sec).

In order to remove the unwanted portions of the photoresist, it must be developed, rinsed, and dried. For example, the photoresist can be developed by contacting with a developing agent (e.g., MF-24A for 90 sec), followed by a Quick Dump Rinse (QDR) with deionized water. Finally, the rinsed wafer can then dry via a Spin Rinse Dryer (SRD). For example, it can be spun for 30 sec @ 500 rpm with a deionized water spray, then 3 min @ 2000 rpm under a $N_2$ gas flow, and finally for 3 min @ 4000 rpm in air to dry.

The quality of photolithography can be verified by optical microscopy to match the desirable percent of defects, desired geometry, and the photoresist free area. If the photoresist is not fully removed, the wafer can be placed in the developer bath (e.g., contacted with MF-24A) for an additional 10-15 sec, then cleaned via the QDR and SRD methods and then checked again by optical microscopy.

Heater and Electrical Lead Deposition:

With the photomask applied, the heater and electrical leads are then formed. One way to achieve thin and uniform layers of heater and/or electrical leads (as well as the other layers/components of the sensor) is via sputtering. Other techniques including atomic layer deposition, chemical vapor deposition, and thermal evaporation can also be used for the heater and electrical leads, as well as for the other layers/components of the sensor.

Optionally an adhesive layer (e.g., Ti or Cr) can be deposited first, followed by the desired material for heater (e.g., Pt, Au, or poly-silicon) and/or electrical lead (Pt and Au). The adhesive layer can be deposited by sputtering using an appropriate target (e.g., a Ti wafer).

An example of the thickness of the optional adhesive layer is about 2 nm. Another example is about 5 nm. Other examples of the thickness of the optional adhesive layer include from about 1, 2, 3, 4, to 5 nm. An example of the thickness of the electrical lead is about 300 nm. Other examples of the thickness of the electrical lead include from about 100, 150, 200, 250, 300, 350, 400, 450, 500, 550, 600, 650, 700, 750, 800, 850, 900, 950, to 1000 nm. An example of the thickness of the heater is about 300 nm. Other examples of the thickness of the heater include from about 100, 150, 200, 250, 300, 350, 400, 450, 500, 550, 600, 650, 700, 750, 800, 850, 900, 950, to 1000 nm.

It can also be desirable to deposit alignment marks to allow for additional photomasks to be aligned. These marks are not limited by shape (e.g., X's, crosses, boxes, etc.) and need only be large enough to be seen when aligning another photomask.

Removing Photomask #1:

Once the electrical leads and heater have been applied, Photomask #1 is removed to allow for the deposition of the metal oxide layer. Photomask #1 can be removed using standard technology. For example, the modified wafer can be placed in an acetone bath for 2 hours at 60-70° C. The wafer can then be placed in a sonicated bath for 5-10 min to remove the remaining metal coated photoresist. An optical microscope can be used for quality control of metal deposition. The thickness of the deposited metal layer can then be verified using a contact profilometer.

Figure 2:
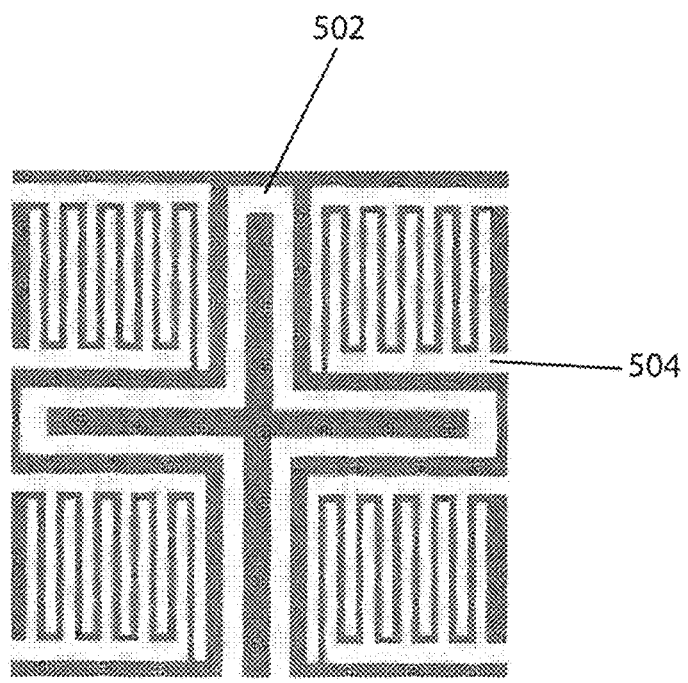
FIG. 2 shows a heating element (area surrounding the "T" in the middle and electrical leads (interdigitated terminals) deposited on a wafer.

FIG. 2 shows an example of a part of a wafer to which a heating element 502 (white area surrounding the "T" in the middle) and electrical leads 504 (interdigitated terminals) (remaining white area) have been deposited and Photomask #1 has been removed. The heater 502 in this figure separates 4 sensor areas.

In another aspect, the heater and electrical leads are different materials, e.g., a poly-silicon heater and Pt leads. If different materials are chosen, then an additional photomasking step will be necessary. Either the heater or electrical leads are applied while the location on the wafer for the other is protected. Photomask #1 is then removed and #1A is applied to allow for the other of the heater or electrical leads to be applied. Photomask #1A is then removed. The structure shown in FIG. 2 could also be an example wherein the heater and electrical leads are different materials.

Applying Photomask #2:

In order to deposit the metal oxide, the heater (and optionally other parts of the wafer) needs to be protected. Photomask #2 can be applied similarly to the Photomask #1. It is useful to be able to align Photomask #2 with Photomask #1. For example, Photomask #1 can have crosses on both sides of the mask and Photomask #2 can have squares.

As with Photomask #1, the quality of photolithography should be verified by optical microscopy to match the geometry and desirable percent of defects. If the developed photoresist is not fully removed, the wafer should be placed again in the developer (e.g., contacted with MF-24A for an additional 10-15 sec), then cleaned via the described QDR and SRD methods and checked again by optical microscopy.

Figure 3:
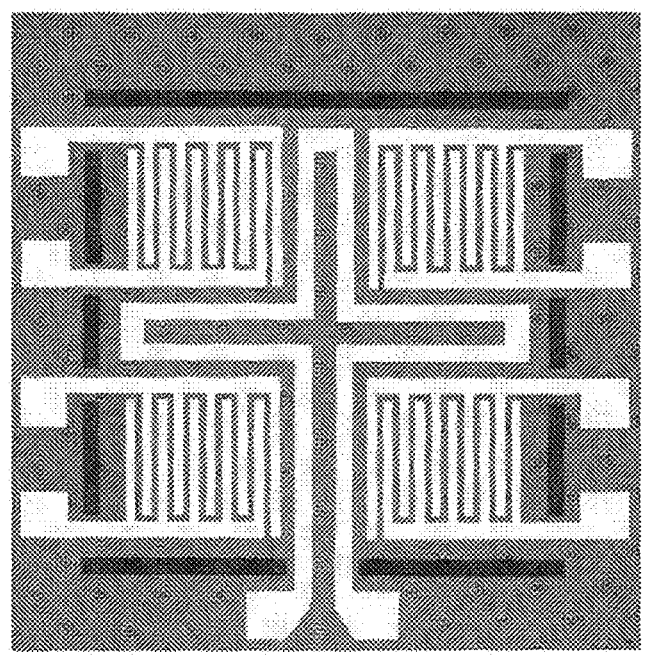
FIG. 3 shows a wafer after trenching (black areas etched silicon) and removal of the photomask. In one embodiment, the wafer is 1.875×1.875 mm.

Trenching:

RIE etching: One way to decrease the power required to heat the metal oxide is to substantially isolate the sensor area from the surrounding wafer. This can be achieved first by HE etching of the $SiO_2$ layer to form a discontinuous trench around the sensor area (see the black lines shown in FIG. 3). The trench is discontinuous as the $SiO_2$ under the electrical leads and heater is not removed. The etched area can be inspected under an optical microscope. The process is repeated if necessary to remove the $SiO_2$ completely in the desired areas.

One way to separate the platforms from the wafer is via etching. For example, the $SiO_2$ from an outline around each platform can be etched as a part of the RIE etching process. This begins the process of creating 624 separate sensor platforms from the original wafer.

Before proceeding to etch part of the silicon layer, it is useful to measure the thickness of the photoresist. If the photoresist thickness is less than 2~µm after RIE, then the photo resist can be removed and reapplied. A thicker photoresist (e.g., SPR 220-7 (provides ~7 µm layer at 4000 rpm)) can be chosen to protect the features from the DRIE etching that is to follow. It can be beneficial to trench with DRIE immediately after removing the $SiO_2$ layer to avoid new oxide formation.

DRIE etching: Prior to DRIE etching, the silicon wafer is protected by attaching a support silicon wafer (e.g., a 500 µm support silicon wafer) to the back side of the silicon wafer. The support wafer protects the processed wafer from being broken in the DRIE chamber. The silicon on the front side of the wafer that was exposed during RIE etching is then etched via DRIE. The etched area is inspected under optical microscope. The process is repeated if necessary to finish removing the unwanted silicon.

If the platforms are to be separated by etching, this process can be continued with the DRIE. For example, the silicon in the outline around each platform formed by the above $SiO_2$ etching can also be etched to continue the process of creating 624 separate sensor platforms from the original wafer.

Removing Photomask #2:

Photomask #2 can then be removed using the lift-off process described for Photomask #1.

Sensing Element Fabrication:

A third photomask (Photomask #3) can be applied similarly to the Photomask #1 and aligned similarly to Photomask #2 (e.g., squares on Photomask #3 can be aligned with crosses from Photomask #1). As with Photomask #1, the quality of photolithography should be verified by optical microscopy to match the geometry and desirable percent of defects. If the developed photoresist is not fully removed, the wafer should be placed again in developer (e.g., contacted with MF-24A for an additional 10-15 sec), then cleaned via the described QDR and SRD methods and checked again by optical microscopy.

With Photomask #3 in place, a metal oxide layer (sensing layer) can be deposited (e.g., via sputtering).

One example of a metal oxide is $SnO_2$. Other examples include $ZnO$, $V_2O_5$, $WO_3$, $TiO_2$. $Al_2O_3$, and $Fe_2O_3$. A useful method of depositing the metal oxide layer is via sputtering. This method allows one to precisely control the thickness of the layer being deposited and also provides a consistent and repeatable process for forming the metal oxide layer (as opposed to methods such as using a sol-gel paste). The metal oxide nanograins are formed during the annealing process (see below).

An example of the thickness of the metal oxide layer is about 36 nm. Other examples of the thickness of the metal oxide layer include from about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, to 50 nm depending on desired the oxide parameters. The thickness of the metal oxide layer can be measured by a contact profilometer.

Figure 4A:
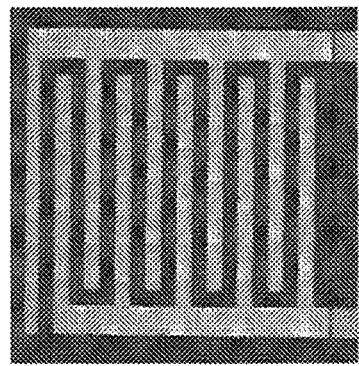
FIGS. 4A-C.
Figure 4B:
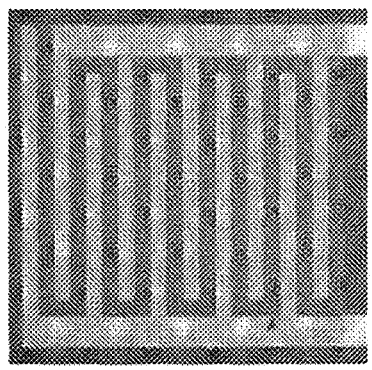
Figure 4C:
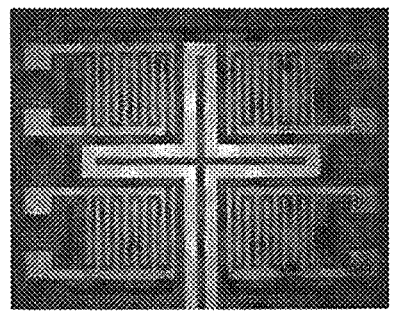

FIG. 4(a) shows a sensor before a metal oxide layer is applied. FIGS. 4(b) and (c) show a sensor and platform, respectively, after a metal oxide layer is applied.

After the metal oxide layer is in place, a dopant layer can then be fabricated on top of it. The dopant layer typically substantially covers the top or exposed side of the metal oxide layer. The dopant nanoparticles are formed during the annealing process (see below).

One example of a dopant is $TiO_2$ (the $TiO_2$ can be sputtered as $TiO_2$ or as Ti and then oxidized via annealing). Other examples include Ti, $TiO_2$, Au, Cu, CuO, $Cu_2O$, Mo, $MoO_2$, $MoO_3$, Ni, NiO, $Ni_2O_3$, Pt, Pd, Ag, AgO, Ru, $RuO_2$, Rh, $Rh_2O_3$, Os, $OsO_2$, $OsO_4$, Ir, and $IrO_2$. The dopant if sputtered as a non-oxide metal (e.g., Ti) is typically, with the exception of Au, Pt, and Pd, oxidized during annealing (see below). This oxidation process oxides part of the dopant (typically the area exposed to oxygen), but does not necessarily oxidize all of the dopant. For example, some of the dopant inside may still be in an unoxidized state. Au, Pt, and Pd, while not forming oxides (e.g., $TiO_2$) during annealing, do form quasi-oxide states on their surfaces (e.g., quasi-stable clusters such as $Pd_nO_m$ and $Pt_nO_m$).

The different combinations of metal oxide and dopant layers provide different sensitivities to different gases. A useful method of depositing the dopant layer is via sputtering. As with the metal oxide layer, sputtering allows one to precisely control the thickness of the nanoparticle layer being deposited and also provides a consistent and repeatable process for forming a nanoparticle layer.

An example of the thickness of the dopant layer is about 8.5 nm. Other examples of the thickness of the dopant layer include from about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, to 15 nm depending on desired the dopant parameters. The thickness of the dopant layer can be measured by a contact profilometer.

With the metal oxide and dopant layers formed, Photomask #3 can be removed as described for Photomask #1.

Different Sensing Elements:

If the sensor platform contains sensors with different metal oxide layers and/or different dopant layers (i.e., different sensors), then the process of applying a photomask, developing it, forming the metal oxide and dopant layers, and removing the photomask is repeated for as many tunes as necessary. For example, if each platform contains 4 different sensors separated by a heater (similar to the structure shown in FIG. 3), then process of applying the metal oxide and dopant layers will be repeated three addition times (Photomasks 3A, 3B, and 3C will be used) to provide a sensor with 4 distinct metal-oxide/dopant sensing areas.

"Floating" Sensor (Membrane) Formation:

After all the sensing elements are deposited and doped, the bottom of the wafer is then etched to remove the $SiO_2$ layer under the sensor area (where the metal oxide and dopant layers are located) as well as a substantial part of the bottom of the silicon layer. For example, if the silicon layer is 200 µm thick, then about 150 µm can be removed, thereby leaving only about 50 µm of silicon under the sensor and creating a "floating" sensor by removing enough silicon to convert the trenches previously formed into openings (i.e. holes). Removal of the silicon and forming the openings reduces the energy needed to power the sensor platform (and resulting integrated sensor).

The features on the top of the wafer should be protected with a layer of photoresist (e.g., photoresist 1813 can be applied). The bottom of the wafer can now be modified.

A photoresist (Photomask #4)(e.g., photoresist SPR 220-7) can be applied onto the backside (unmodified side) of the wafer similarly to previous photomasks. After exposure to UV light and developed, the photomask is complete and etching can begin. Photomask #4 is typically thicker than Photomasks #1-3 because of the amount of silicon being removed during the DRIE process. As a result, more time is usually required to allow the thicker photoresist layer, e.g., 4-10 µm to cure.

The bottom $SiO_2$ layer can be removed via RIE. The etched area is then inspected under optical microscope. The process is repeated if necessary to remove the oxide completely.

If the platforms are to be separated by etching, this process can be continued with the RIE on the bottom of the wafer. For example, the $SiO_2$ on the bottom of the wafer that is under the outline formed above around each platform can also be etched to continue the process of creating 624 separate sensor platforms from the original wafer.

Next part of the silicon layer is removed via DRIE. It can be beneficial to start DRIE right after removing the oxide to avoid new oxide formation over time.

Due to the harsh conditions of the DRIE process, the silicon wafer can first be protected by attaching a support silicon wafer (e.g., a 500 μm support silicon wafer) to the top side of the silicon wafer. The support wafer protects the processed wafer from being broken in the DRIE chamber. Once the top of the silicon has been protected, silicon from the bottom can then be etched, e.g., ~150 μm, via DRIE. The etched area is inspected under optical microscope. The process is repeated if necessary to complete removal of the desired amount of silicon.

If the platforms are to be separated by etching, this process can be completed with the DRIE on the bottom of the wafer. For example, the silicon in the outline around each platform formed by $SiO_2$ etching on the bottom can also be etched to complete the process of cutting all the way through the wafer and of creating 624 separate sensor platforms from the original wafer.

With the removal of $SiO_2$ and silicon complete, Photomask #4 can be removed as described for Photomask #1.

The amount of silicon removed from under the sensing area depends on the desired thickness of the "floating" sensor. One example of the thickness of silicon under the sensing area is 50 μm. Other examples include from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38,39, 40, 41, 42, 43, 44, 45, 46, 47, 48, 49, 50, 51, 52, 53, 54, 55, 56, 57, 58, 59, to 60 μm.

Figure 5:
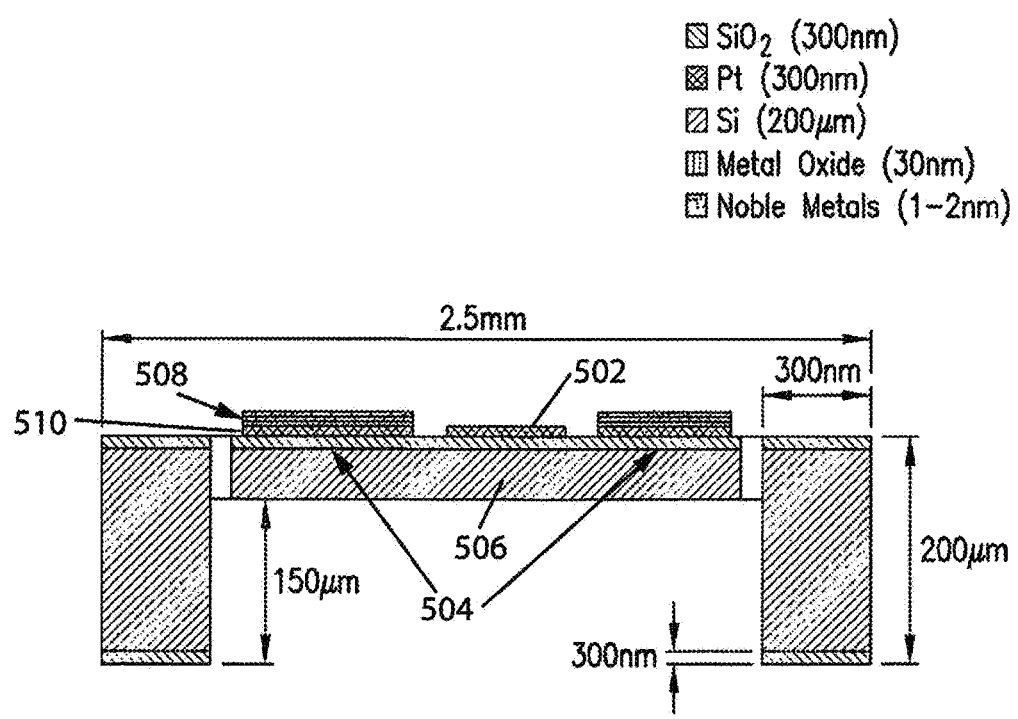
FIG. 5 shows an example of a "floating sensor" (which can also be referred to as a membrane with $SiO_2/Si/SiO_2$ connectors).

An example of the "floating" sensor of the present invention is shown in FIG. 5. which shows a heating element 502, interdigitated electrical leads 504, a membrane 506, a dopant layer 508 and a metal oxide layer 510. The dark lines on either side of the Pt leads represents discontinuous openings (holes) in the wafer that were created by the RIE/DRIE trenching and then RIE/DRIE removal of the bottom side of the wafer.

The depth of the DRIE is typically such that it cuts apart the platforms without the need for mechanical cutting. Optionally, one can reduce the depth of the DRIE etching and then cut the platforms apart mechanically.

Sensor Packaging:

Bonding conditions: Gold wire diameter 25 μm, substrate temperature 130° C., tail 2, loop 2. Kulicke & Soffa Wire bonder Model 4500: (a) First bond (ball bond): force 2, power 2, time 2; (b) Second bond (wedge bond): force 3, power 2.5, time 2.

Figure 6A:
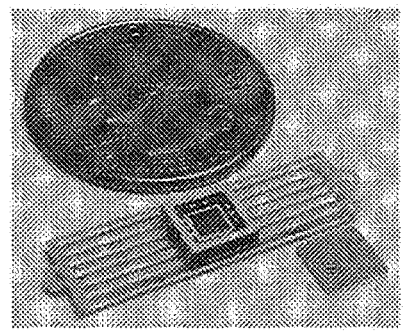
FIGS. 6A-C.
Figure 6B:
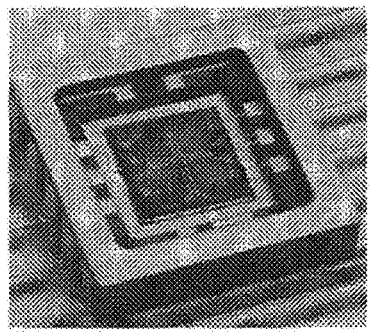
Figure 6C:
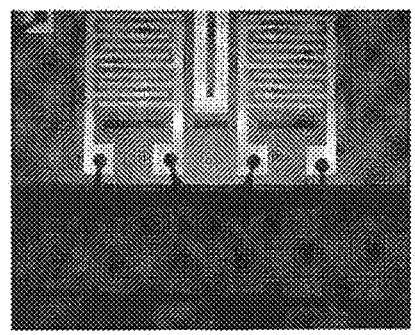

With the sensor platform complete, it is then connected to a package in order to be incorporated into an integrated chemical sensor. The surface of each sensor's platform has to be leveled with the package pin holders in order to improve the bonding contacts and prevent the wire from breaking or being stuck inside the soldering capillary. The sensors cup (see FIG. 6 (a)) are attached in order to complete the integrated sensor package.

Sensor Annealing:

In order to form the metal oxide into nanograins and the dopant into nanoparticles, and if necessary to oxidize the dopant, the sensor is annealed in the presence of oxygen (e.g., air or synthetic air). The annealing can be conducted prior to packaging. However, a benefit of annealing after packaging is that the platform need not be touched post packaging.

Annealing temperature: 200-900° C., including 200, 250, 300, 350, 400, 450, 500, 550, 600, 650, 700, 750, 800, 850, to 900° C.

Annealing time: 1-40 hours, including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, to 40 hours.

Annealing atmosphere: an oxygen-containing gas, including air and synthetic air.

The temperature chosen is dependent up on the components of the sensor and its desired use. The size of the grains/particles and their morphology can be observed via SEM (scanning electron microscope), AFM (atomic force microscope), and/or XRD (x-ray diffraction).

During the annealing process metal oxide grains (nanograins) are formed from the amorphous, sputtered structure. The size of the grains 5-20 nm impacts the sensitivity of the sensor.

During the annealing process the dopant, if not already oxidized (e.g., Ti sputtered as opposed to $TiO_2$), oxides and dopant nanoparticles are formed. The formation of dopant nanoparticles causes the continuous amorphous layer (e.g., formed via sputtering) is crystallized to form a polycrystalline structure.

In one example, the annealing temperature for $SnO_2$ is 700° C., for 4 hours.

In one example, the annealing temperature for ZnO is 700° C., for 4 hours.

EXAMPLE 2

$H_2S$ sensor

Step 1: Starting Substrate

A 4" diameter oxidized silicon (100) wafer (200 μm with a 300 nm $SiO_2$ top (polished) and bottom layers) was prepared by washing with deionized water (DI water) and then inspected under an optical microscope.

Step 2: Top Side Photolithography (Photomask #1)

To provide patterns for the heater and terminals, a photomask (photomask #1) was applied to the wafer using photolithography. Photoresist 1827 (a positive photoresist) was applied to the polished side of the wafer. The wafer was spun (Laurel EDC-650-23B Spin Processor) for 0.2 sec@ 500 rpm while the photoresist was applied, and then for 10 sec @ 4000 rpm.

After spin coating, the wafer was "soft baked" by heating at 90° C. in air for about 70-75 sec. The "soft baked" wafer was then exposed to UV light 325W for about 22 seconds, followed by a toluene bath (60 sec), blow drying with $N_2$, and another soft baking (this time 90° C. for about 15 sec).

The photoresist was developed by contacting with MF-24A for 90 sec, followed by a Quick Dump Rinse (QDR) in DI water with the DI water being changed 3 times. Finally, the rinsed wafer was then dried via a Spin Rinse Dryer (SRD) by being spun for 30 sec @ 500 rpm with a DI water spray, then 3 min @ 2000 rpm under a $N_2$ gas flow, and finally for 3 min @ 4000 rpm in air to dry. The quality of photolithography was verified by optical microscopy to match the geometry and desirable percent of defects.

Step 3: Terminals and Heater

Ti (adhesive layer, ~2 nm). Deposition parameters: 5 mTorr (Ar), DC power 500W, time 30 sec.

Pt (~300 urn). Deposition parameters: 5 mTorr (Ar), DC power 200W DC, time 15 min.

Both the Ti and Pt targets were loaded into the sputter chamber of a Lesker PVD 75. The Ti (adhesive layer) was first applied using the above parameters. In order to avoid oxidation of the Ti layer, Pt was deposited immediately after the Ti deposition.

Step 4: Photoresist Removal

Following sputtering, the modified Si wafer (now with electrical leads and a heater) was placed in an acetone bath for 2 hours at 60-70° C. and then in an ultra-sonicated bath for 5-10 min to remove the remaining metal coated photoresist. An optical microscope was used for quality control of metal deposition. The thickness of the deposited metal layer was verified using a contact profilometer.

A random analysis of Ti/Pt contacts and heaters on different places (platforms) on the wafer revealed small thickness variation between 295-306 mu due to uneven coating.

Step 5: Top Side Photolithography (Photomask #2)

A second photomask (Photomask #2) was applied similarly to the first photomask with the exception that the toluene bath and dry and soft bake steps were not performed. A Suss MA6 mask aligner was used to align Photomask #2 with Photomask #1. In order to align Photomask #2 with Photomask #1, alignment marks on both masks are positioned at the same place. Photomask #1 left crosses on two sides of the mask. Photomask #2 had squares to be aligned with the crosses. As with Photomask #1, the quality of photolithography was verified by optical microscopy to match the geometry and desirable percent of defects.

Step 6: Silicon Oxide Reactive Ion Etching (RIE)/RIE etching: $H_2+CH_4$ (5+5 sccm), Pressure (500 mTorr), RF power (80 W), time (10 min). The silicon oxide layer was etched via RIE using the above parameters (see the black lines shown in FIG. 3). The etched area was inspected under optical microscope. The $SiO_2$ from an outline around each platform (i.e., columns and rows on the wafer) was also etched to begin the process of creating 624 separate sensor platforms from the original wafer.

Step 7: Deep Reactive Ion Etching (DRIE) of Silicon/ DRIE of silicon parameters: passivated phase and etching phase ~50 cycles: (a) Passivated phase: C4F8 flow rate 200 sccm for 5 sec; and, (b) Etching phase: SF6 flow rate 400 sccm for 15 sec.

The DRIE was performed following oxide removal to avoid new oxide formation. The silicon wafer was first protected by attaching a 500 μm support silicon wafer to the bottom of the silicon wafer being process. The support wafer protects the processed wafer from being broken in the STS DRIE chamber. The silicon on the top side of the wafer was then etched via DRIE using the above parameters. The etched area was inspected under optical microscope.

The silicon in the outline around each platform formed by $SiO_2$ etching was also etched to continue the process of creating 624 separate sensor platforms from the original wafer.

Photomask #2 was removed using the lift-off process of step 4.

Step 8: Top Side Photolithography (Photomask #3)

A third photomask (Photomask #3) was applied similarly to Photomask #2. Photomask #3 was aligned with Photomask #1, similarly to Photomask #2.

The quality of photolithography was verified by optical microscopy to match the geometry and desirable percent of defects.

Step 9: Metal Oxide Deposition

Parameters for deposition: RF Power 200W, time 15 min, base pressure (ultimate pressure before the deposition): $5\times10^{-6}$ Torr, process pressure (Ar pressure during the deposition): 12 mTorr, sputtering material ($SnO_2$ target) 4 inch diameter, distance between source ($SnO_2$) and sample holder (sensor's platform)~5", sample holder rotation speed 30 rpm.

A $SnO_2$ target was loaded into the sputter chamber and a 36 nm layer was $SnO_2$ was deposited. The thickness of metal layer was controlled by an Inficon thickness sensor. The thickness of the oxide layer was measured by contact profilometer.

Step 10: Dopant Deposition

Parameters for the deposition: RF Power: 250W, time 20 min, base pressure (ultimate pressure before the deposition) $5\times10^{-6}$ Torr, process pressure (Ar pressure during the deposition) 12 mTorr, sputtering material ($TiO_2$ target) diameter 3 inch, distance between source ($TiO_2$) and sample holder (sensor's platform) ~6", sample holder rotation speed 30 rpm.

The $TiO_2$ target was loaded into the sputter chamber and an 8.5 nm layer of $TiO_2$ was deposited. The thickness of metal layer was controlled by an Inficon thickness sensor. The thickness of the oxide layer was measured by contact profilometer.

The sample was placed into a room temperature acetone bath for 15 min and then dried by a medium flow rate nitrogen gun. During this process all the PMMA (photoresist) and unnecessary oxide were removed. As a result, only the sensing areas were left covered with metal oxide and dopant.

Step 11: Bottom Side Photolithography (Photomask #4)

After all the sensing elements were deposited and doped, a thin layer of positive photoresist 1813 was spin coated (0.5 sec @ 500 rpm, 10 sec @ 4000 rpm) on the top of the wafer to protect the now formed sensors from damage.

Photoresist SPR 220-7 (Photomask #7) was spun coated onto the bottom (unmodified side) of the wafer. The wafer was spun for 0.2 sec@ 500 rpm while the photoresist is applied, and then for 10 sec @ 4000 rpm. After spin coating, the wafer was "soft baked" in air by heating at 115° C. for about 90 sec, with a 30 sec temperature ramp to 115° C. The "soft baked" wafer was then exposed to UV light 325W for 35 seconds and then allowed to sit for at least 35 minutes (post exposure time). After sitting the wafer was baked again at 115° C. for about 90 sec, with a 30 sec temperature ramp to 115° C. The photoresist was then developed by contacting with MF-24A at 21° C. for 60-80 sec, followed QDR (as described above), and SRD (as described above).

Step 12: Bottom Side RIE

RIE etching: $H_2+CH_4$ (5+5 sccm), Pressure (500 mTorr), RF power (80 W), time (10 min).

The $SiO_2$ layer on the bottom of the wafer is etched via RIE using the above parameters. The etched area is then inspected under optical microscope.

The $SiO_2$ on the bottom that was under the outline formed above around each platform was also etched to continue the process of creating 624 separate sensor platforms from the original wafer.

Step 13: Bottom side DRIE/DRIE of silicon parameters: passivated phase and etching phase ~150 cycles: (a) Passivated phase: C4F8 flow rate 200 sccm for 5 sec; and, (b) Etching phase: SF6 flow rate 400 sccm for 15 sec.

The silicon wafer was protected by attaching a 500 μm support silicon wafer to its top side. The silicon on the bottom side of the wafer was then etched, ~150 μm, via DRIE using the above parameters. The etched area was inspected under optical microscope.

The silicon in the outline around each platform, formed by $SiO_2$ etching on the bottom, was also etched to complete the process of cutting all the way through the wafer and of creating 624 separate sensor platforms from the original wafer. After etching, the 624 newly formed sensor platforms are transferred via a 100 mm diameter one sided circle scotch tape.

Step 14: Sensor Packaging

Figure 7A:
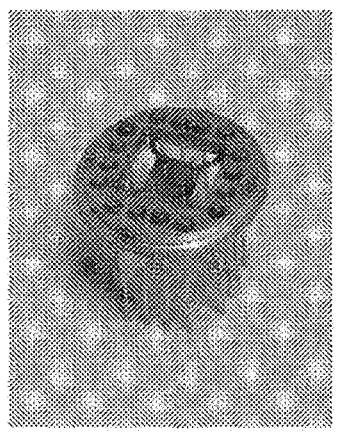
FIGS. 7A-C.
Figure 7B:
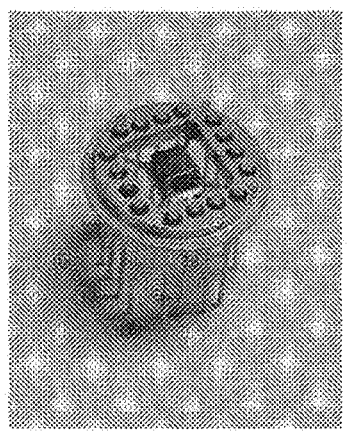
Figure 7C:
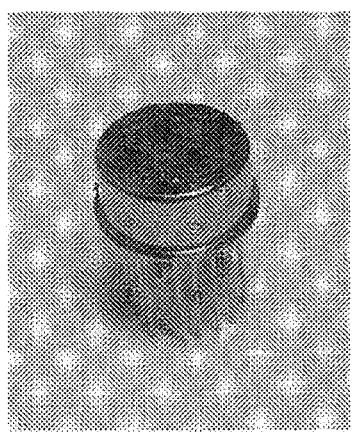

The transistor outline (TO) package was prepared for the sensing platform attachment. The supported structure (FIG. 7a) was prepared by an Othermill-Compact Precision CNC+ PCB Milling Machine. One of the previously prepared sensor platforms was then attached to the package with die attach ultra-high temperature paste and then annealed at 170° C., 1 atm, for 15 min to cure the paste. The electrical connection between the transistor outline package and the sensor platform was made by using S&F wire bonder with 1 mill golden wire (FIG. 7b). Finally, the cup for passive gas detection was fabricated from the cup for the transistor outline package by using the Othermill milling machine. The cup was then attached to the package (FIG. 7c).

Step 15: Annealing

Figure 8:
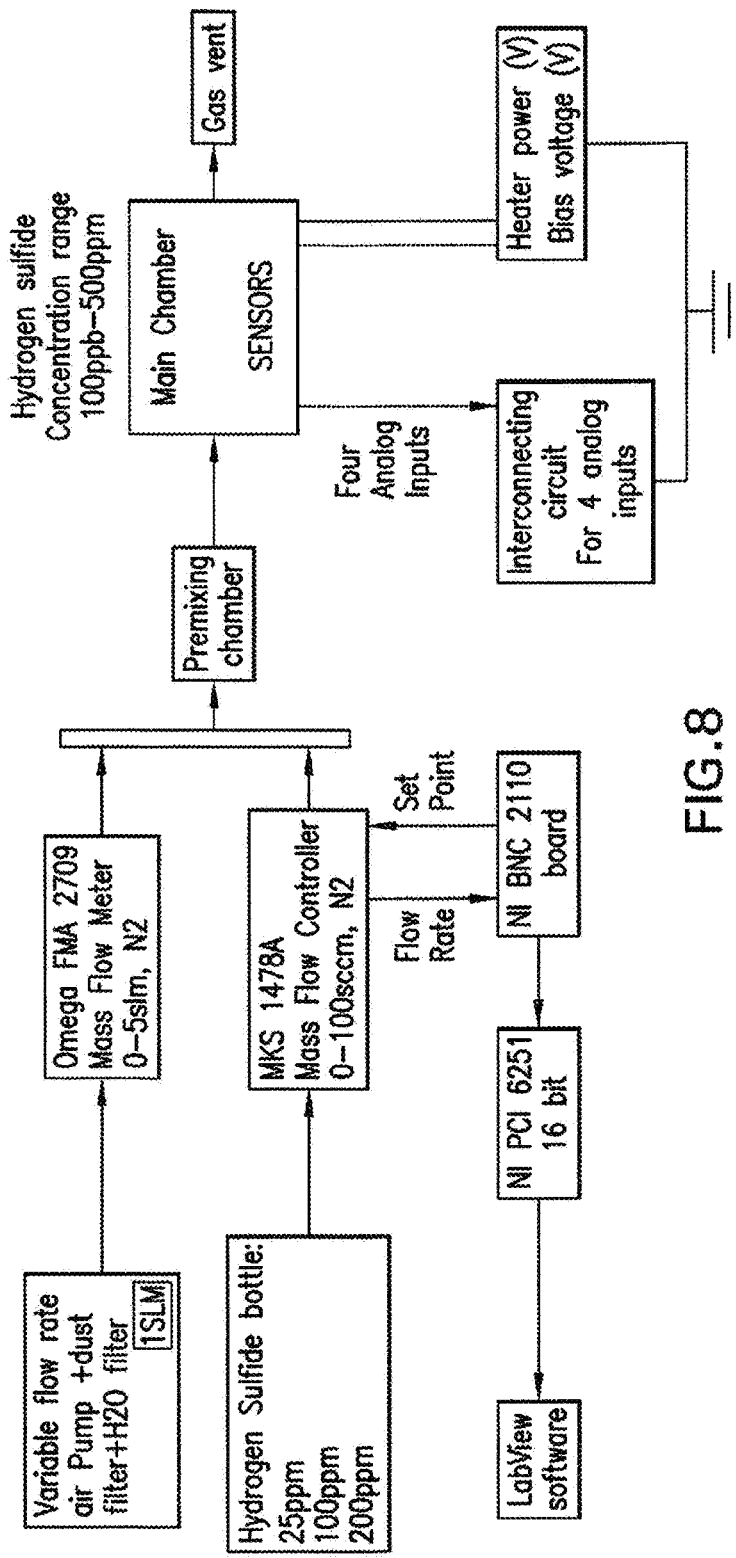
FIG. 8 shows a gas delivery and data collection system for prototype testing and development.

The sensor was imported into a gas calibration system (see description below). The power for the platform heater was adjusted to match the surface temperature of the sensing element near 250° C. The annealing process was performed for 24 hours inside the main chamber (FIG. 8). After annealing, the sensor is calibrated.

Figure 9:
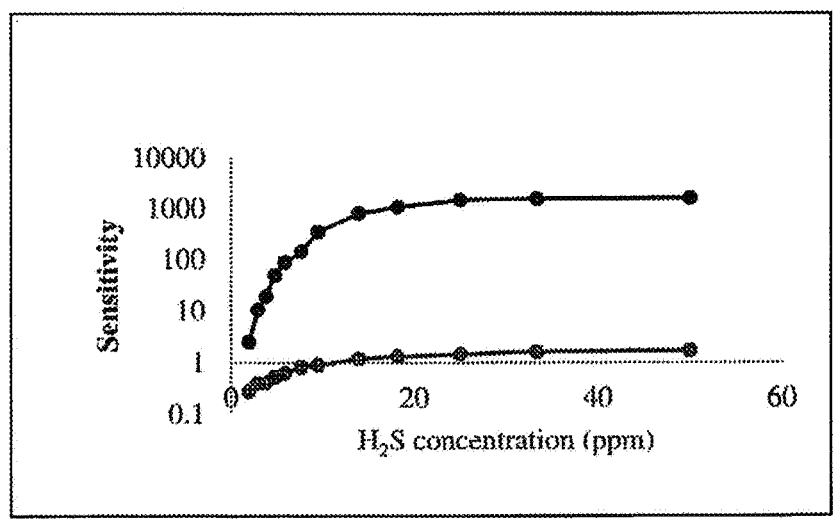
FIG. 9 shows the sensitivity vs. concentration of $SnO_2/TiO_2$ sensor and MQ136 commercial $H_2S$ sensor.

Calibration:

Calibration data was obtained for 2, 3, 4, 5, 6, 8, 10, 15, 20, 25, 30 and 50 ppm $H_2S$ using the gas delivery system and data collection system shown in FIG. 8. The results are shown in FIG. 9.

Sensor Performance:

Sensor characterization has been divided into several main categories, which are usually used to evaluate the sensor performance: sensitivity, selectivity, stability, time of response and recovery, and power consumption.

Sensitivity:

Sensitivity is defined as a normalized change in conductivity of the sensor element due to the gas (e.g., $H_2S$) exposure. The sensitivity of the sensor was measured over different ranges of concentrations. The result was compared with a commercially available sensor for hydrogen sulfide MQ136. The sensitivity of the $SnO_2/TiO_2$ of the present invention was found to be three orders of magnitude greater than MQ136 (FIG. 9).

Figure 10:
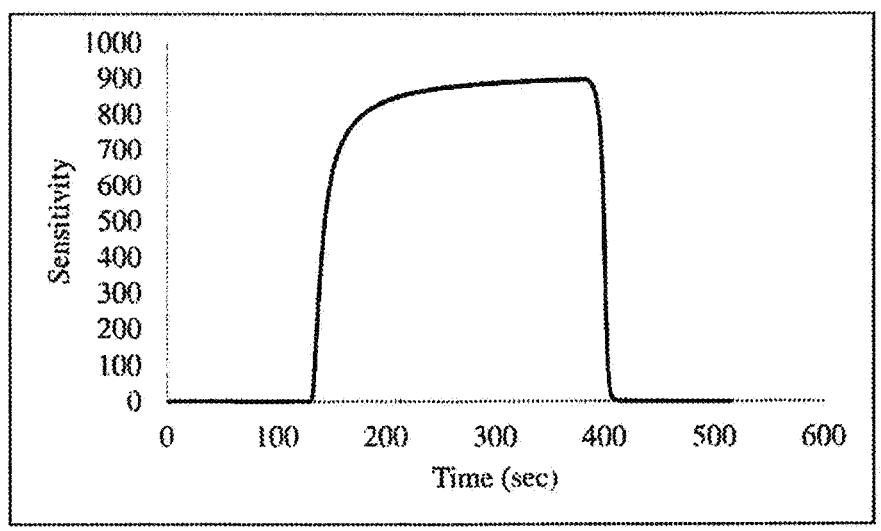
FIG. 10 shows the sensitivity vs. time response of the $SnO_2/TiO_2$ sensor to 50 ppm of $H_2S$.

The sensitivity versus time response of the $SnO_2/TiO_2$ of the present invention is shown in FIG. 10.

Figure 11A:
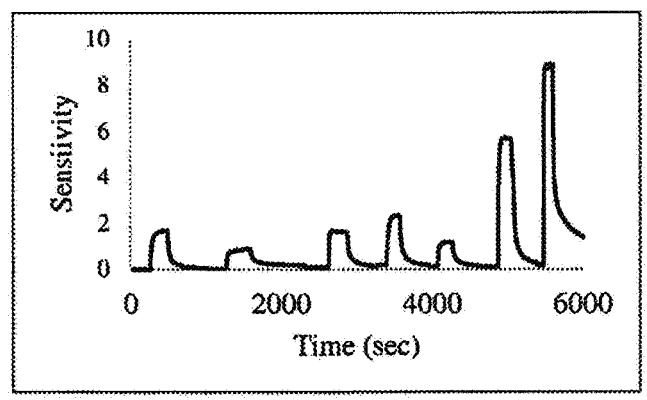
FIGS. 11A-B.
Figure 11B:
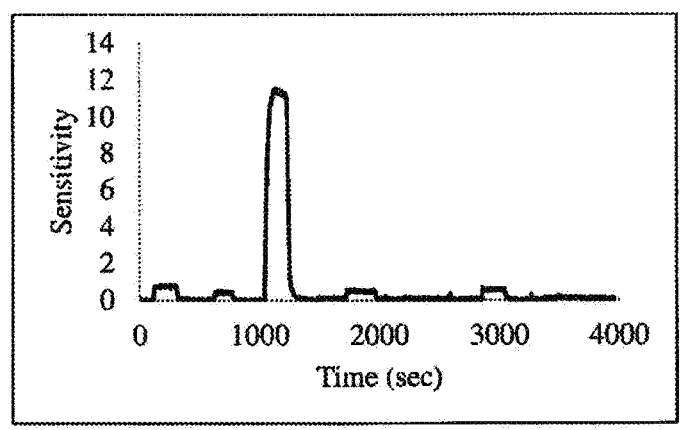

Selectivity:

The sensor's selectivity determines by the ability of the sensor respond selectively to a specific analyte or a group analytes. During the selectivity studies several different analytes with various concentrations were used to determine the selectivity of the $SnO_2/TiO_2$ sensor of the present invention compared to the commercial sensor MQ136. As can be seen, the present sensor is much more selective towards $H_2S$ than MQ136 (FIGS. 11(a) and (b)). FIG. 11A shows Ethanol (15 ppm), $H_2S$ (4 ppm), CO (100 ppm), Toluene (10 ppm), Benzene (10 ppm), Propane (0.1%), and Methane (4%), respectively. FIG. 11B shows Ethanol, Toluene, $H_2S$, CO, Methane, Benzene, and Propane, respectively (all at the same concentrations as in FIG. 11A).

Figure 12:
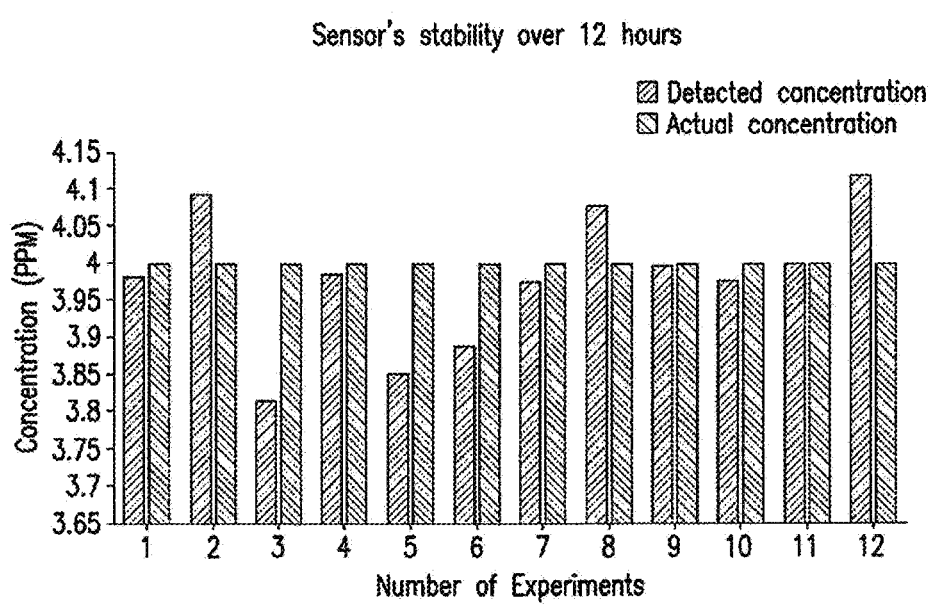
FIG. 12 shows the sensor stability over 12 hours with one test/hour and exposure to 4 ppm $H_2S$.

Stability:

The stability of a sensor is related to its ability to detect an unknown concentration of $H_2S$ after calibration. An error analysis was performed in order to guarantee (99% confidence) that the actual value obtained is located within a particular interval/range (+/−error ppm). The stability studies were performed by exposing the sensor to 4 ppm $H_2S$ over 12 hours, with sampling once an hour. The results are shown in FIG. 12.

Time Response and Recovery:

Preliminary evaluation shows that the disclosed sensor has much shorter response and recovery time than the commercial sensor MQ136.

Figure 13A:
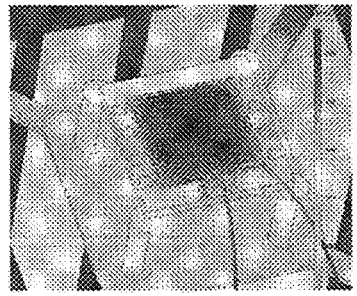
FIGS. 13A-C.
Figure 13B:
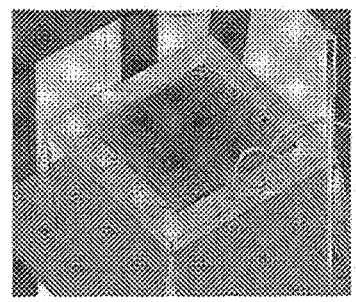
Figure 13C:
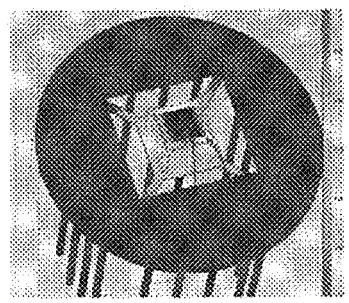
Figure 14A:
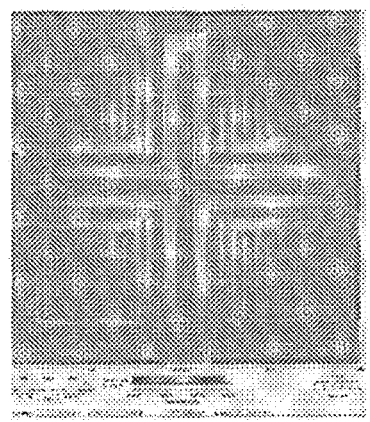
FIGS. 14A-B.
Figure 14B:
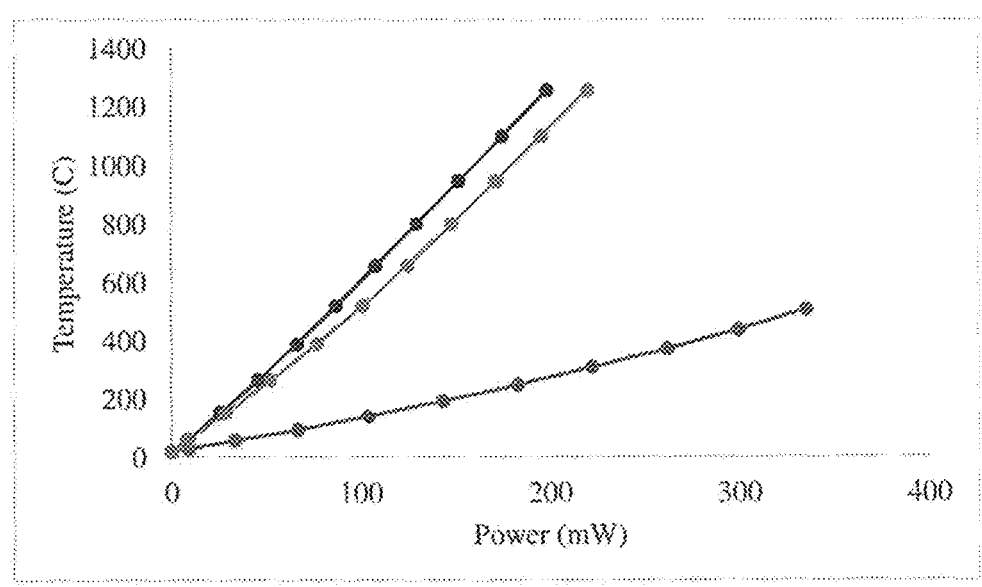

Power Consumption and Temperature Distribution:

Minimization of power consumption is extremely important for portable sensors. The suspended $Si/SiO_2$ membrane structure of the present invention was developed for high temperature localization and thermal insulation. In addition to that the TO package can be modified (and was in this example) in order to decrease the power consumption and decrease the heat transport from the sensing platform to the electronic package. Two modifications of the TO package were simulated using Comsol 5.0 software (FIG. 13) and then manufactured and tested under a Quantum Focus Instruments (QFI) thermal imaging system, which is able to capture thermal images and video of the platform featuring 0.1° C. temperature and 5 μm spatial resolutions (FIG. 13(a)).

By using a Comsol simulation, power consumption was significantly reduced by using a different platform geometry. The total power can be below 20 mW per sensor with a 2×2 mm and 100 μm thick sensor platform.

EXAMPLE 3

Integrated Chemical Sensor:

An integrated chemical sensor (ICS) can be assembled using the platform packaged into a transistor outline as its sensor. The integrated sensor, further comprises: (a) a resistor network, comprising: a load resistor electrically connected to the sensors of the packaged sensor platform; and, (b) a logic element (e.g., transistor or a computer) electrically connected to the resistor.

Alternatively, in addition to the platform packaged into a transistor outline as its sensor, the ICS further comprises: (a) a resistor network, comprising: a load resistor electrically connected to the sensors of the packaged sensor platform; and, (b) an analog-to-digital converter (ADC), the ADC being electrically connected to the resistor network (e.g., can be attached to an explorer board); (c) a logic element (e.g., transistor or a computer) electrically connected to the ADC (e.g., electrically connected to the explorer board, if present); and, (d) optionally a gas delivery (sampling) system (present for active gas delivery).

The computer used for the ICS can also be called a micro-computer or microcontroller. A microcontroller is a small computer on a single integrated circuit containing a processor core, memory, and programmable input/output peripherals. Examples of a microcontrollers/micro-computers include the Raspberry Pi computers (e.g., Raspberry Pi 2 or 3).

The reactivity of the sensors (observed as a change in their conductivity) to a gas being sampled (e.g., air) can be measured by wiring the sensor platform in series with a load resistor to create a resistor network. As the conductivity of each sensor changes, in response to the composition of the gas being measured, the voltage at the center node of the resistor network changes. The analog voltage signal from the resistor network can be converted to a digital signal using an analog-to-digital converter (ADC) located on an explorer board. The explorer board is the link between the hardware (e.g., sensor platform) and the computer (e.g., a microcomputer). One example of a computer is the Raspberry Pi computer. This computer utilizes Linux software to execute commands written in Python, a computer programming language. The Raspberry Pi executes the Python code which controls the explorer board and all attached hardware.

Figure 15A:
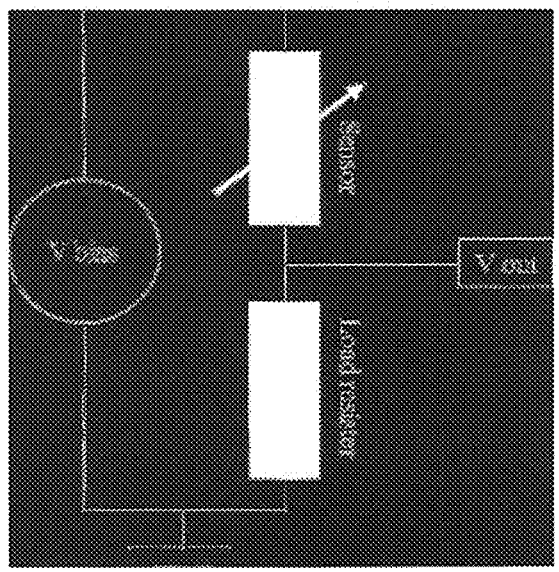
FIGS. 15A-C.
Figure 15B:
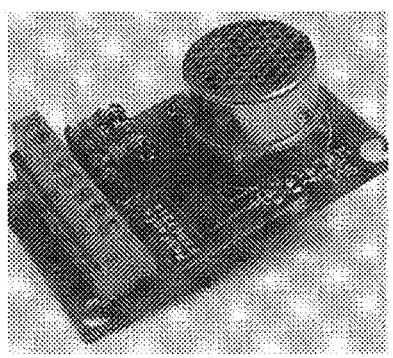
Figure 15C:
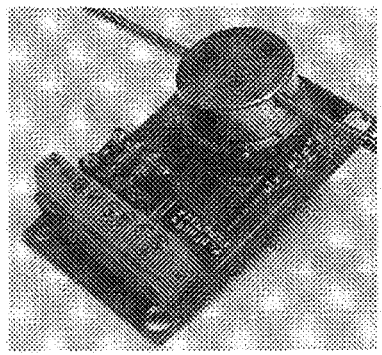
Figure 16:
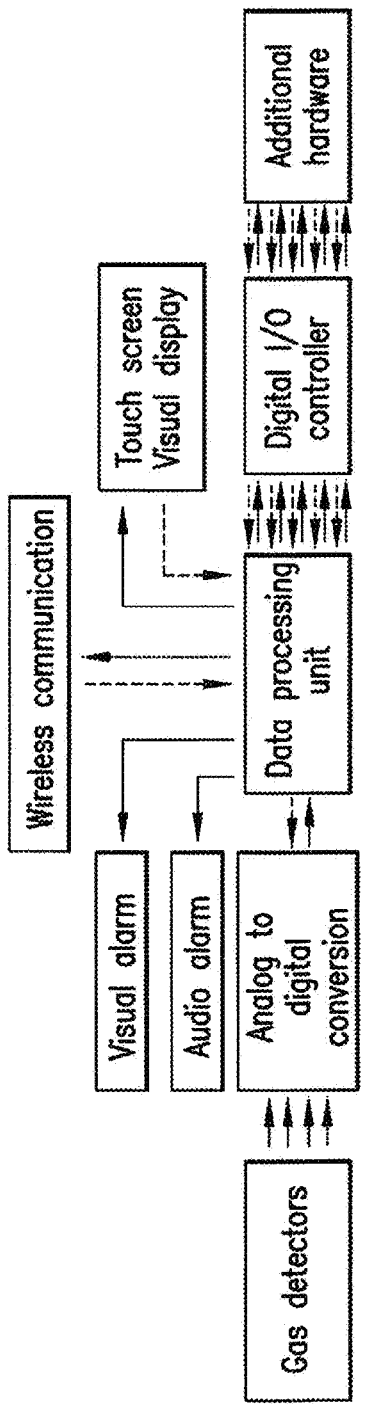
FIG. 16 shows a schematic of data processing and hardware communication.

Data Collection:

The data collection process was built around a divided voltage circuit (see FIG. 15(a)). The main idea of the circuit is to detect the change in current through the sensor (e.g., each sensor on a sensor platform) during gas (e.g., air) exposure. The change in current can be detected by using a load resistor. In order to achieve maximum sensitivity and a wide detection range, the load resistor should be as low as possible, since it is used for current measurements across it in a way similar to the classical ammeter. The lowest limit of the load resistance is determined by the A/D (analog/digital) resolution of the computer (e.g., microcontroller). Any signal that is lower than the A/D resolution cannot be detected by the microcontroller and will be interpreted as zero. The sensor stability determines how close the load resistance can be to its lowest limit in order to avoid sudden drops below A/D resolution. The higher the stability, the closer to A/D resolution the load resistance can be. In the present invention, the value of the load resistor is chosen in such a way that the baseline of the sensor ($V_{out}$) is 10 times higher than the A/D resolution of the system. For example, if the system has a 10 bit A/D converter then the resolution of the system with 5V bias voltage is approximately 5 mV and the baseline of the system is 50 mV ($V_{out}$). In order to optimize the system performance, it is desirable to filter out the white noise from the signal. White noise significantly affects the lowest detection limit of the sensor. In order to filter out the white noise, a low-pass filter over 100 points was applied to each of the analog channels (sampling rate is 10 Hz per channel). The low-pass filter is a signal processing code filtering out high-frequency components and preserving low-frequency components of the signal. A mechanical filter can also be used instead of the software filter.

For active mode sampling (see below), the explorer board controls the vacuum pump and solenoids to collect gas samples and deliver them to the sensor platform (i.e., the gas sensing element(s)). Once the data is collected (see above) and analyzed by the micro-computer (see below) the resulting information can be communicated to a user via a direct display (e.g., an LCD touchscreen panel mounted near the sensor or another type of lighted display). Alternatively or additionally, the resulting information can be communicated via Wi-Fi, Bluetooth and/or a network. The integrated chemical sensor can be capable of alerting users at any location with available internet accessibility. The device can also be modified to provide users with proximity dependent notifications on Bluetooth equipped devices.

Wireless communication and signaling can be an important and useful part of the integrated chemical sensor. In one example, the ICS is equipped with both USB Wi-Fi and Bluetooth modules. The Linux software running on the Raspberry Pi can use these modules to communicate with sensors at remote locations. The modules can also be used to push data to nearby equipped devices using Bluetooth or Wi-Fi thus allowing remote devices and databases to alert users of changes in the system. An XBee module can be connected to the GPIO pins to allow the device to communicate with existing sensor networks in industrial or home kitchen equipment.

An XBee module is a wireless communication module that communicates in the 2.4 GHz band over the "Zigbee" protocol.

GPIO is a term for General Purpose Input/Output pins. These are connections on a microcontroller or other digital device that can be used to both input and output data.

Data Analysis:

The input signal for analysis and pattern recognition can be used in the following form:

$$\text{Signal} = \text{Sensitivity} = \frac{I(t) - I_{baseline}}{I_{baseline}} = \frac{V(t) - V_{baseline}}{V_{baseline}}$$

$I(t)$, $V(t)$—current and voltage values at the moment t.

$I_{baseline}$ and $V_{baseline}$ are the baseline values of current and voltage in the clean air.

For a chemical sensor, steady state response assumes that upon the exposure, the output signal reaches an equilibrium state (plateau). In contrast to steady state response, transient response assumes non-equilibrium state upon the exposure (rising or declining characteristics). Extracted features for the steady state response (amplitudes) and extracted features for the transient response (signal derivatives, parameters of exponential curve fitting and fast Fourier transforms) were used as input data for pattern recognition algorithm. Linear Discriminant Analysis (LDA) was found to be a useful algorithm.

In the multidimensional hyperspace of sensor outputs, the LDA is used to find a projection which minimizes within class variance while maximizing the distance between the classes. In other words, the coordinate system is transformed in order to minimize the scattering within a single class and maximize inter-class scattering. This was accomplished by finding a coordinate transformation, which maximizes Fisher's criteria. Responses were then projected onto the Fisher basis vectors to obtain discrimination.

Figures 17A, 17B:
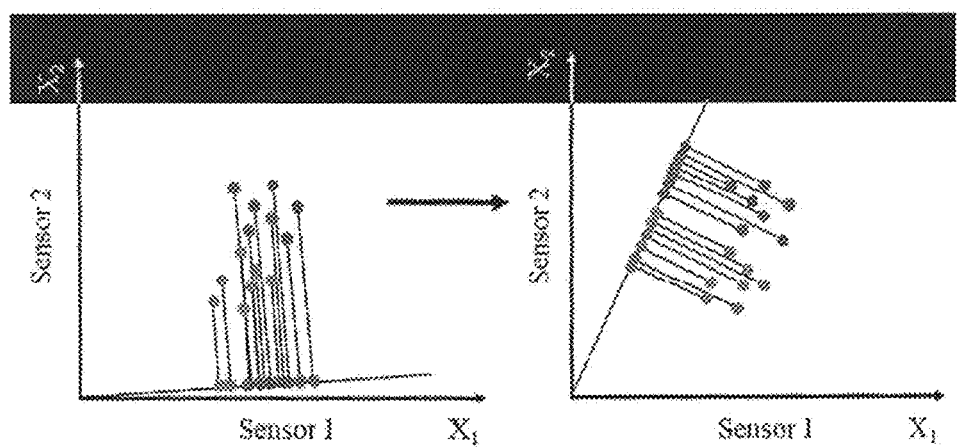
FIGS. 17A-B show an Illustration of Linear Discriminant Analysis.

FIGS. 17A-B illustrates an example of an LDA analysis for the hypothetical system of two sensors analyzing two substances. Odor sensors 1 and 2 respectively record amplitudes x1 and x2 for a single odor, which are graphed as coordinates (x1, x2) in a 2D plot. Shown in the plot are 7 measurements each of two odors, A and B, which are done to improve the statistics that are needed to provide better identification and discrimination between odors A and B. The set of 7 measured points A(x1, x2) of odor A and the 7 measured points of B(x1, x2) of odor B are then projected onto a straight line, where the line passes through the origin (FIG. 17A). This projection line is then rotated about the origin to an optimal angle (FIG. 17B). At the optimal rotation angle, the projection of the 7 points A(x1, x2) and 7 points of B(x1, x2) onto the rotated projection line, then produces the largest separation between the group of projected points for odors A and B. The largest separation between measured points for odors A and B are characterized by a particular rotated projection line, where (1) the centers or means of the measured set of points of odors A and B have the largest separation, and (2) the spread or standard deviation of the measured set of points of odors A and B are minimum. That is, maximizing the distance between the mean of the project points for odors A and B, and minimizing the respective standard deviation of the projected points of odors A and B about their respective means, thereby increases the likelihood of successful identification and discrimination of odors A and B.

Gas Sampling:

The sensors of the present invention can be used in a passive or active mode. A passive mode assumes that the sensor is placed in the ambient air without a special sampling system for air delivery. This method provides an accurate detection and concentration measurement at a certain point in space (e.g., smoke alarm).

Figure 18:
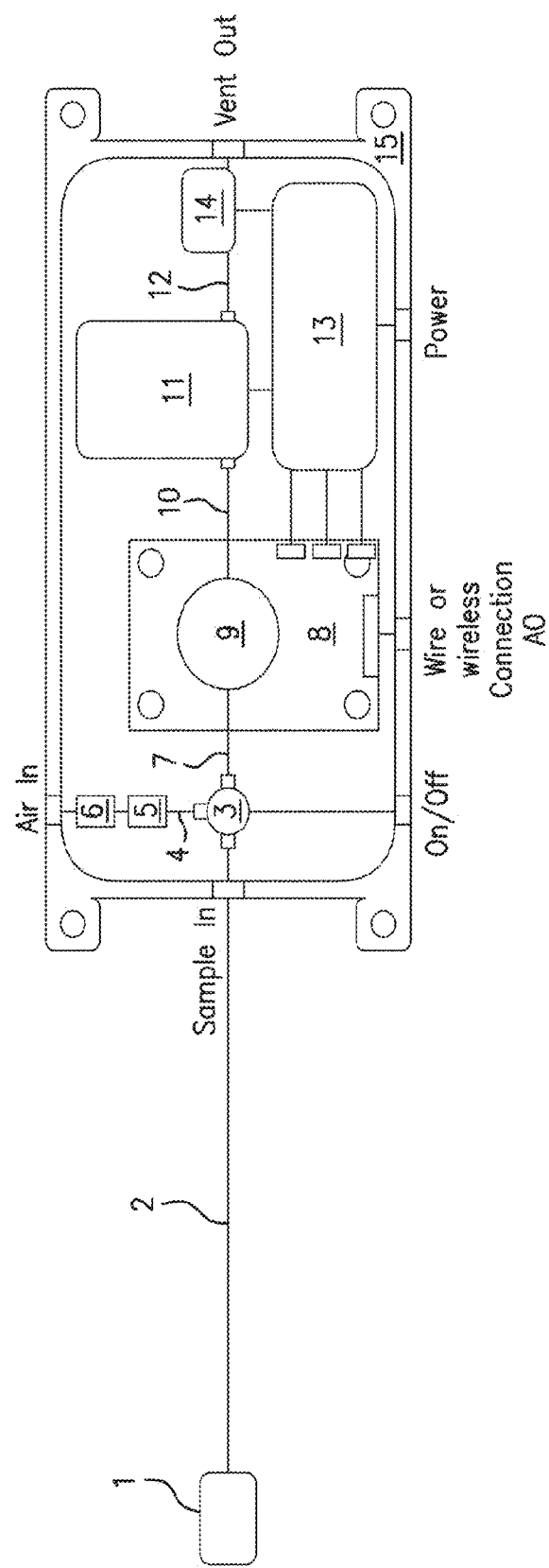
FIG. 18 shows an active sample delivery system.

The active mode assumes the presence of a sampling system for active air intake/delivery. FIG. 18 shows an example of an active sample delivery system. In FIG. 18, 1=sample collector, 2=⅛" tube, 3=3-way solenoid valve, 4=⅛" tube, 5=humidity filter, 6=dust filter, 7=1/16" tube, 8=electronic circuit, 9=main chamber, 10=1/16" tube, 11=mass flow controller, 12=1/16" tube, 13=power supply, 14=micropump, and 15=aluminum shielding box.

Parts for the active sample delivery system are commercially available, though aluminum shielding box 15 will typically need to be custom made. The electronic circuit is a divided voltage circuit for four sensors with four analog outputs, power supply inlets (0-5V), and IR or bluetooth wireless data transmission modules are optionally included.

Examples of other parts include: (a) ⅛" plastic tube: part number TBGM101 from NResearch. (b) Three way solenoid valve: part number 161K030 from NResearch. (c) Moisture trap and dust filter: ABEST Stainless Steel Airbrush Mini Air Filter Spray In-line Moisture Trap available from Amazon. (d) 1/16" nickel tube: part number TNI140-21 from VICI. (e) Main chamber: The chamber was made out of two parts: part number CAN00804, and part number HDR00823 from Spectrum Semiconductors, Inc. (f) Mass flow controller: part number 3810DS11 from KOFLOC Kyoto. (g) Power supply: AC/DC unit 110VAC to 5V and 3.3V available from AliExpress. (h) Micro pump: part number T3CP-1HE-06-1SNB available from Parker Hannifin Precision Fluidics Division.

The active delivery system is needed to evaluate an average concentration of the analyte of interest over a volume of interest by creating a constant air flow through the sensor platform and then introducing a gas sample in to the main stream for a limited amount of time. The gas sample concentration represents an average concentration over a volume of space at which the sample was taken.

The sample collector can be mobile or stationary. For a mobile collector, the sample inlet would travel around the volume of space collecting the sample for a known time period. For a stationary collector, the network of many inlets has to be designed in order to collect the sample equally from the volume of space.

EXAMPLE 4

Figure 19:
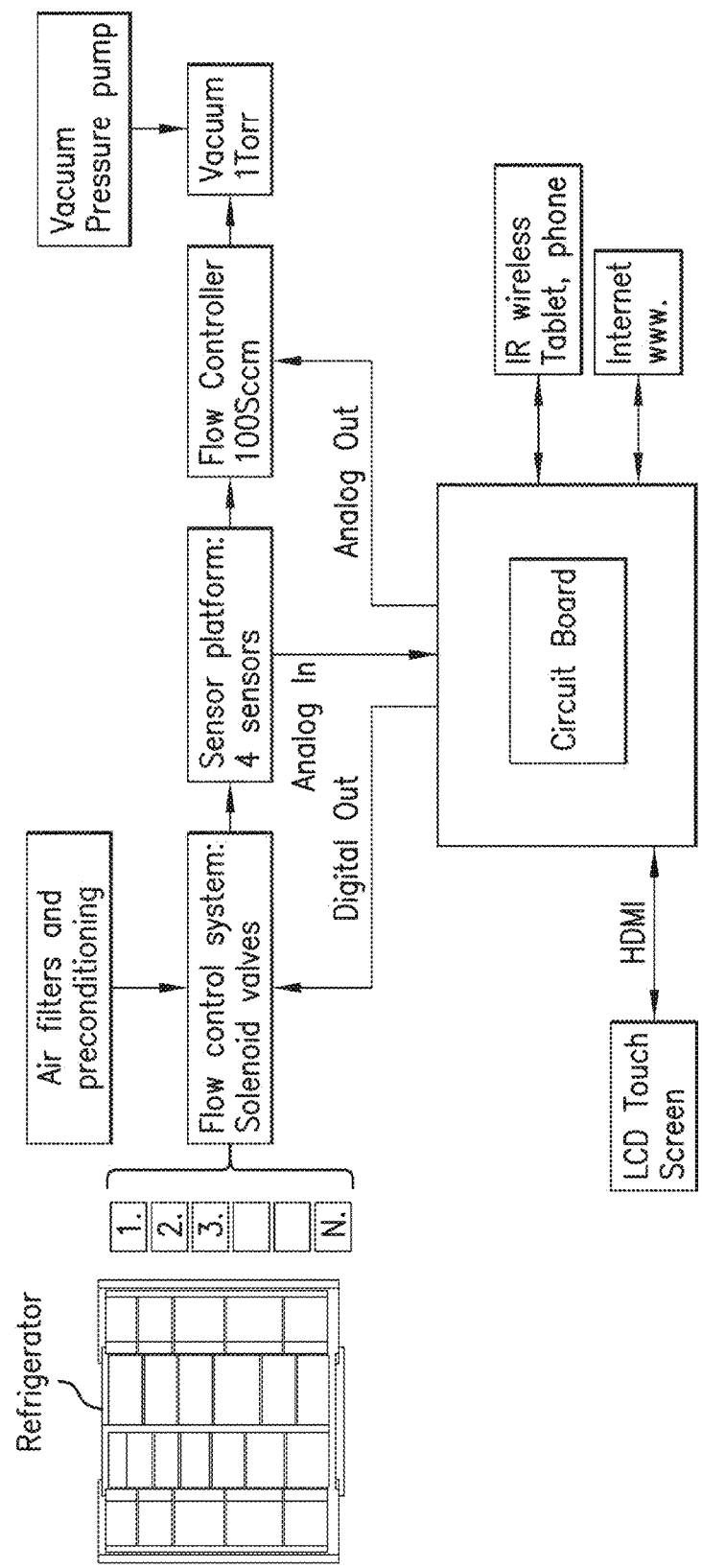
FIG. 19 shows a refrigerator sensor.
Figures 20A, 20B, 20C:
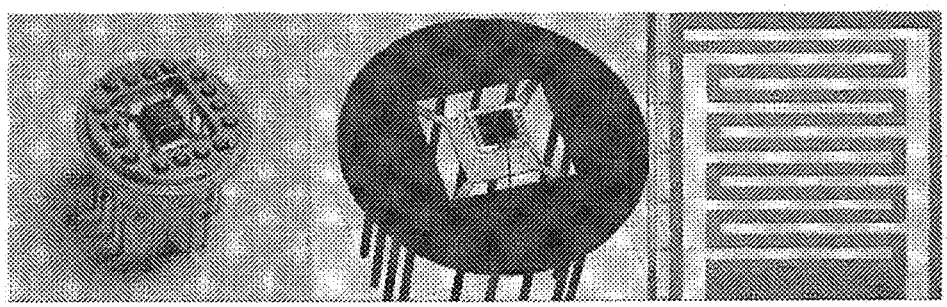
FIGS. 20A-E.
Figure 20D:
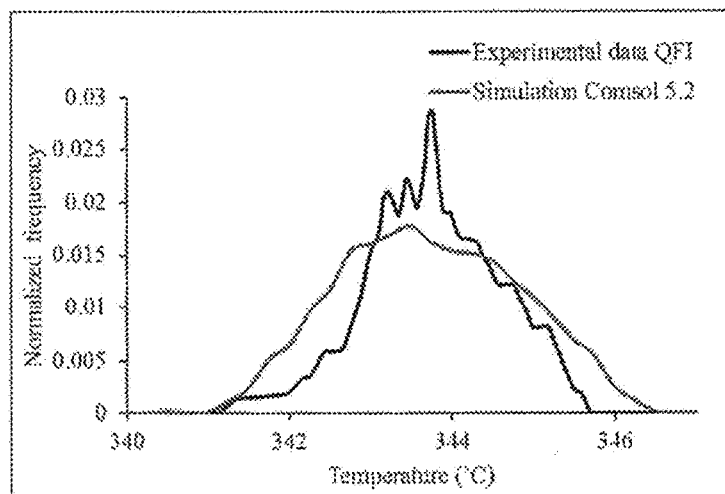
Figure 20E:
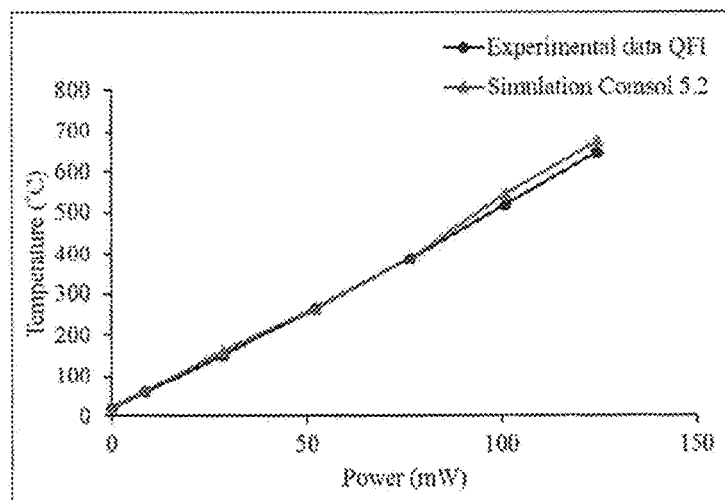

Refrigerator Sensor:

The present sensors can be used to monitor gases in a refrigerator (see, for example, FIG. 19). By connecting at least one platform of sensors to a computer and at least a system that delivers air samples from the refrigerator or clean/filtered air, the sensor platform(s) can be used to monitor the air quality in a refrigerator and as a result the level of spoilage in the refrigerator.

The refrigerator monitoring unit, comprises: a sensory system (comprising: at least one sensor platform), a computer, an explorer board, and an air sampling system. The air sampling system, comprises: (a) at least one air channel connected to at least one storage sections of the refrigerator (e.g., a plurality of air channels, each one connected to a storage section); (b) a "clean channel" for delivery of filtered air from the outside of the refrigerator; and, (c) a flow control unit, comprising: a system of solenoid valves.

The computer (e.g., a micro-computer/micro-controller such as a Raspberry Pi computer) sequentially opens and closes solenoid valves allowing air from the refrigerator storage sections to flow over the sensory system (e.g., the sensor platform) for a defined period of time (e.g., for 1 min). Each sampling cycle is typically followed by flushing the system with air from the "clean channel" (e.g., filtered air) for a defined period of time (e.g., 1 minute), allowing the sensory system to reset its baseline. The air flow through the sensory system will typically remain constant at all the stages of the cycle in order to preserve the stability of sampling conditions. Operation of the sampling system together with signal processing and pattern recognition will be controlled by the computer. The output of the recognition algorithm (e.g., LDA, described above) for each of the storage sections can be displayed on a screen (e.g., LCD screen), located on the door of the refrigerator (or elsewhere if not built into or onto the refrigerator). Alternatively or also, the output can be accessible remotely through a mobile application.

The sensor platform of the present invention can be wired in series with a load resistor to create a resistor network. As the conductivity of the sensor changes, due to the composition of measured gases, the voltage at the center node of the resistor network changes. The analog voltage signal from the resistor network can be converted to a digital signal using an analog-to-digital converter (ADC) located on the explorer board. The explorer board is the link between the hardware and the computer. A Raspberry Pi computer (if used) utilizes Linux software to execute commands written in Python, a computer programming language. The Raspberry Pi executes the Python code which controls the explorer board and all attached hardware. The explorer board controls the vacuum pump and solenoids to collect gas samples from various refrigerator storage sections and deliver them to the sensor platform. Once the data is collected and analyzed by the computer, any indication of food spoilage and its associated refrigerator region can then be communicated to a display. This information can be communicated to the user via methods including: an LCD (e.g., 7" in diameter) touchscreen panel mounted on the exterior of the refrigerator door or an internally mounted color-coded LED indicator lighting located in the region of the refrigerator containing the spoiled food. The computer can also be compatible with WiFi and/or Bluetooth networks and can also be capable of alerting users at any location with available internet accessibility. The device can also be modified to provide users with proximity dependent notifications on Bluetooth equipped devices.

EXAMPLE 5

Bi-Layer and Multi-Layer Sensors:

A MEMS (micro-electrical-mechanical system)-based suspended membrane with a cross-shaped heating element and interdigitated sensor electrodes was fabricated for precise temperature control over an interactive metal oxide layer. The microplatform contains four identical square sensor elements in the corners and a cross-shaped heater in the center of the platform.

The sensor was cleanroom fabricated by a multi-step procedure (all of which are described above): (a) photolithography, (b) sputtering deposition, (c) liftoff, (d) back side photolithography, (e) reactive ion etching, (f) deep reactive ion etching, and (g) cutting apart the sensors.

The heating element and interdigitated sensor electrodes were made out of 300 nm platinum deposited by magnetron sputtering (PVD 75 Lesker). A 5 nm buffer layer of titanium was deposited prior to platinum deposition for better adhesion. The membrane structure was fabricated by Deep Reactive Ion Etching (DRIE). The membrane thickness of 50 μm was verified by surface profilometer KLA-Tencor Alpha-Step IQ. The surface temperature on the suspended membrane was first simulated using Comsol 5.2 software and then compared with the experimental data from Quantum Focus Instruments (QFI) thermal imaging system, which is able to capture thermal images of the platform featuring 0.1° C. temperature and 5 μm spatial resolutions. The microplatform temperature profiles were obtained for different values of power dissipation across the heating element. It was found that the temperature gradient along the sensing element area does not exceed 5° C. when the average surface temperature is above 350° C.

Figure 21A:
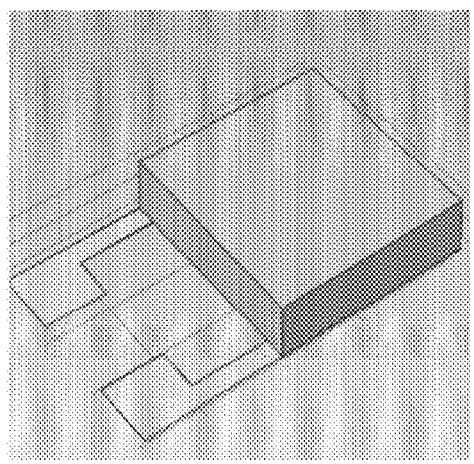
FIGS. 21A-C.
Figure 21B:
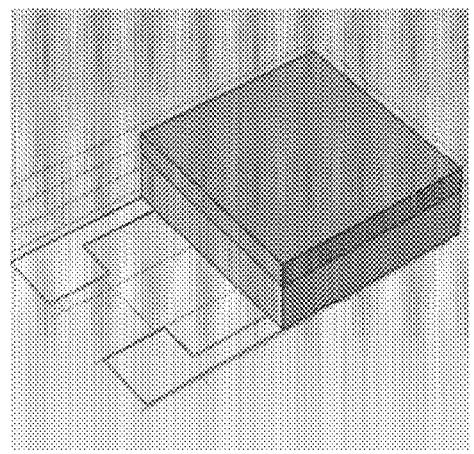
Figure 21C:
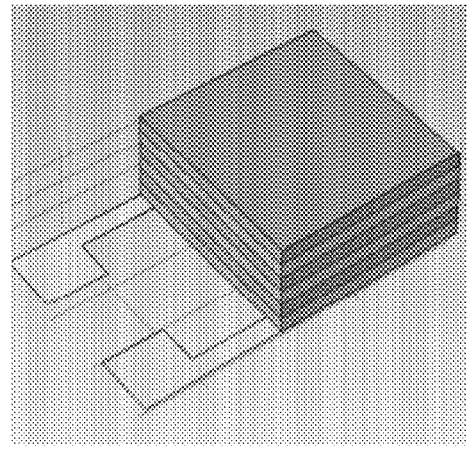
Figure 22:
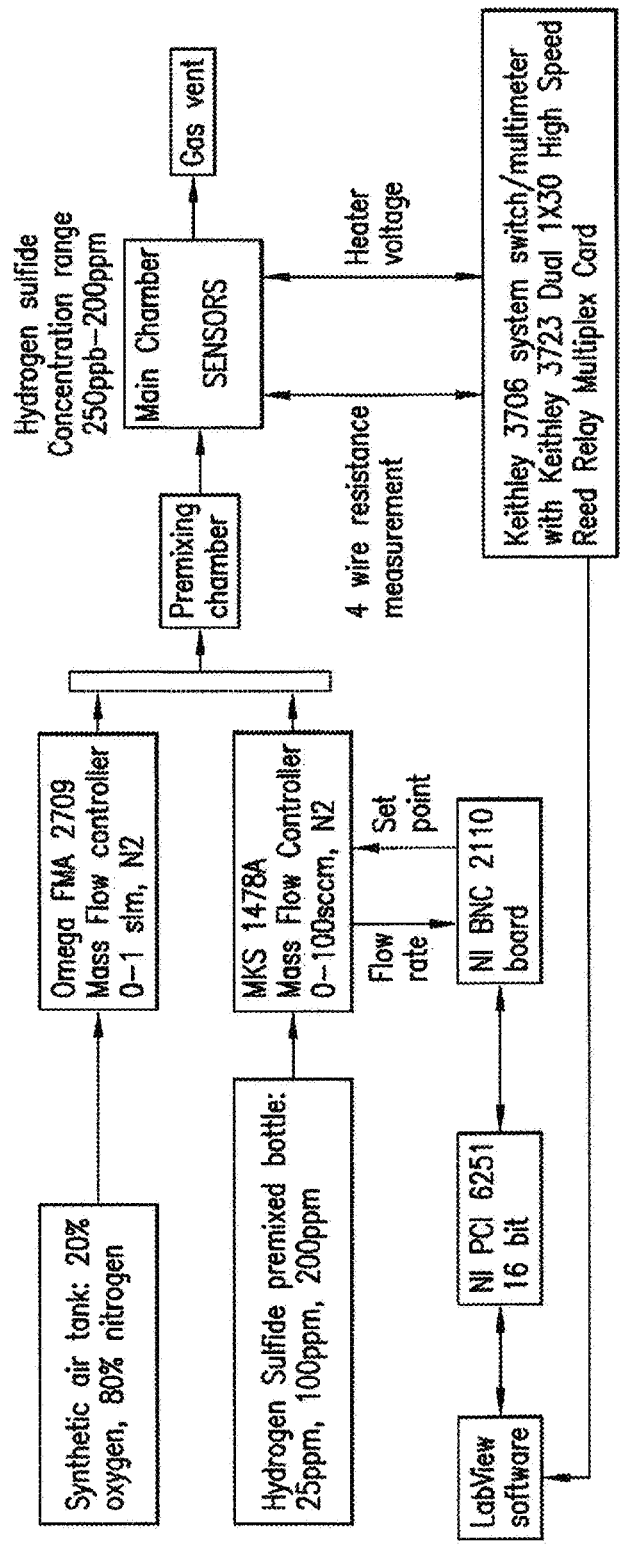
FIG. 22 shows a gas delivery and data collection system.

Thin films of $TiO_2$, $SnO_2$, $SnO_2/TiO_2$ multilayer structure, and $SnO_2/TiO_2$ bilayer structure were deposited by RF magnetron sputtering using $SnO_2$ and $TiO_2$ three inch targets with purity of 99.99% and 99.998%, respectively. The sample rotation speed during the deposition was set up to 30 rpm for equal thickness distribution across the sample area. The deposition was conducted at room temperature and no special bias voltage was applied to the wafer. The schematics of a single-layer, a bilayer and a multilayer are shown in FIGS. 21(a), (b) and (c), respectively. The single-oxide samples ($SnO_2$, $TiO_2$) were sputtered under 12 mTorr of argon (Ar) pressure and RF power 200 W. The bilayer samples of $TiO_2/SnO_2$ were fabricated during the two step process: main layer deposition ($SnO_2$) and surface doping layer deposition ($TiO_2$). The multilayer $TiO_2/SnO_2$ structures were prepared by sputtering alternating layers of the two metal oxides. Different volume contents of $TiO_2$ in $SnO_2$ were obtained by varying power of the $TiO_2$ source during its deposition phase. The multilayer structure was constructed out of a total of 6 layers: 3 layers of $SnO_2$ and 3 layers of $TiO_2$. After the deposition, the total thickness of each sample was verified by surface contact profilometer (KLA-Tencor 500 Alpha-Step IQ). Eight different sample structures were prepared (Table 2). After the deposition, all the samples were annealed in a tube furnace (MKS OTF 1200x) under 500° C. for 48 hours in ultra-zero grade air (UZ300 Airgas 100 sccm).

TABLE 2

Types of structures used in the experiments

| Sensing material | Composition | Total thickness | Sample number |
|---|---|---|---|
| $SnO_2$ | 100% | 30 nm | S0 |
| $SnO_2/TiO_2$ bilayer | 30 nm + 5 nm | 35 nm | S1 |
| $SnO_2/TiO_2$ bilayer | 30 nm + 8 nm | 38 nm | S2 |
| $SnO_2/TiO_2$ bilayer | 30 nm + 20 nm | 50 nm | S3 |
| $SnO_2/TiO_2$ multilayer | 5% $TiO_2$ | 31.5 nm | S4 |
| $SnO_2/TiO_2$ multilayer | 10% $TiO_2$ | 33 nm | S5 |
| $SnO_2/TiO_2$ multilayer | 20% $TiO_2$ | 36 nm | S6 |
| $TiO_2$ | 100% | 30 nm | S7 |

The crystal structure of samples was evaluated by X-ray diffraction method (XRD). The XRD spectrum of samples was collected by a Thermo ARL (model X IRA) X-ray diffraction machine (Cu Kα radiation wavelength was 0.15056 nm). A scanning electron microscope (SEM Zeiss Supra 35) was utilized to study the surface microstructure of the samples. The chemical composition of the samples was obtained by Energy Dispersive X-Ray Spectroscopy (EDAX) analysis. The band gap and work function of tin oxide and titanium oxide were evaluated by UV visible spectrometer AvaSpec-ULS2048L-EVO and Kelvin probe measurement, respectively.

Sensor response characterization was conducted in a small (1 $cm^3$) environmental chamber. The total flow rate through the chamber was fixed at 100 scan during the experiment. All the data was collected under atmospheric pressure. The sensor resistance was measured with the Keithley 3706 system switch/multimeter connected to a PC through Labview interface. The resistance of the sensor was measured with a sample rate of 10 Hz. A system of mass flow controllers (Omega GMA 2709 and MKS 1478A) interfaced with Labview through PCI NI 6251 and BNC21110 was utilized to produce specific concentrations of the target gas. The gas delivery system was able to produce different concentrations of hydrogen sulfide in a range from 125 ppb to 200 ppm. The exposure time was chosen to be 4 min. During this time, the sensor signal was able to reach the saturation point for a particular concentration. After exposure, the chamber was flashed with 100 sccm of clean dry synthetic air until the sensor signal returned to its original baseline. The sensor response was defined as $S=R^{Air}/R^{Gas}$, where $R^{Air}$ is the sensor resistance in clean dry air and $R^{Gas}$ is the sensor resistance upon exposure to hydrogen sulfide.

Figure 23A:
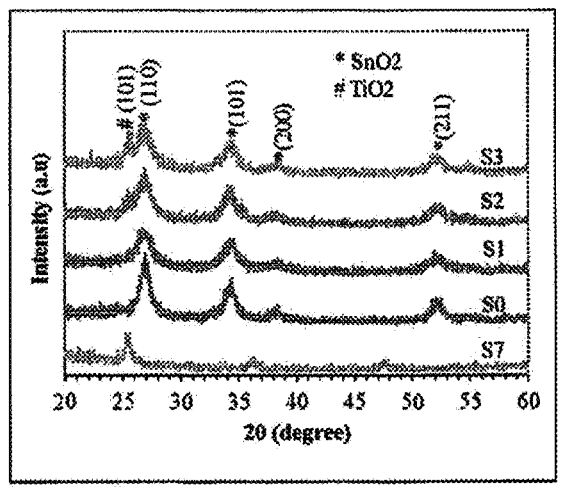
FIGS. 23A-C.
Figure 23B:
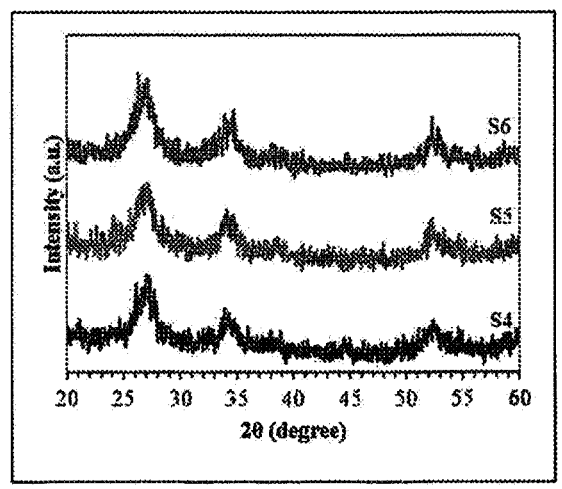
Figure 23C:
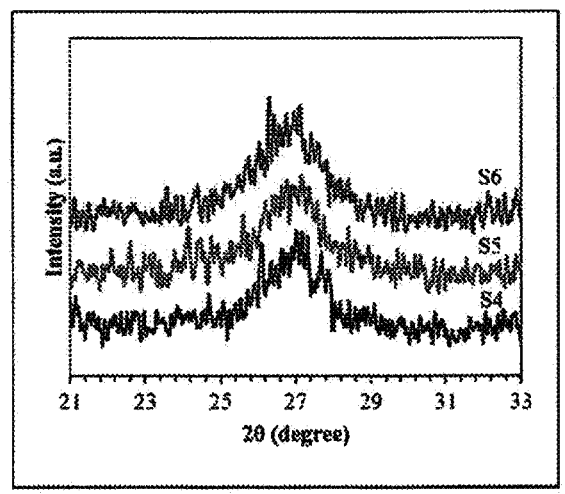
Figure 24A:
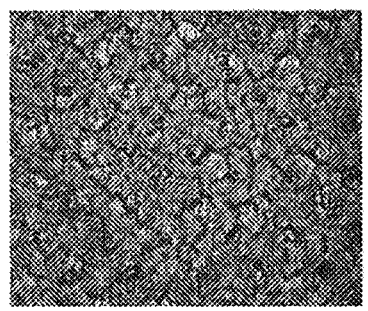
FIGS. 24A-H.
Figure 24B:
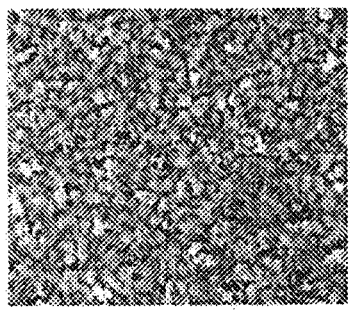
Figure 24C:
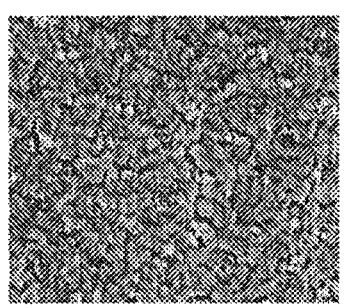
Figure 24D:
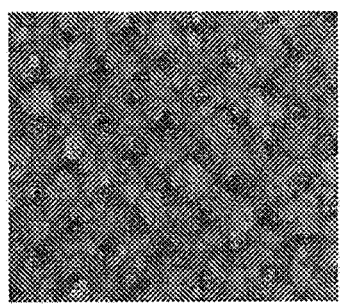
Figure 24E:
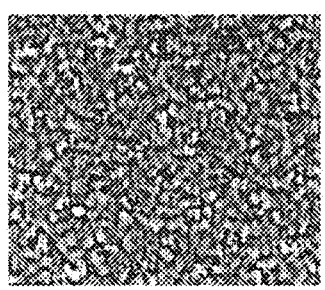
Figure 24F:
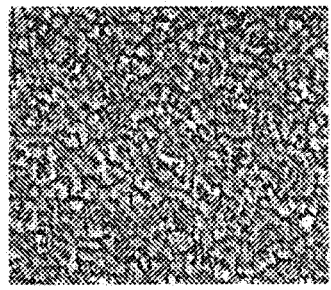
Figure 24G:
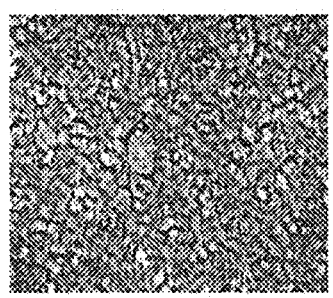
Figure 24H:
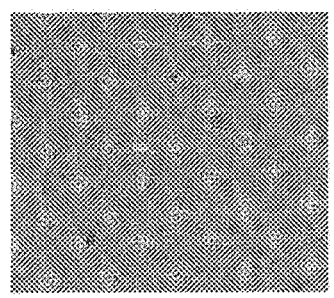

As a result of the above-described annealing, a nanocrystalline structure of oxides was observed by X-ray diffraction (XRD). The XRD patterns were recorded at a scanning rate of 1.2 times per second and a scanning step size of 0.02°. The scanning range for all the samples was from 20° to 60°. FIG. 23 shows the XRD pattern of all the samples (S0-S7). The XRD spectrum of pure $SnO_2$ (S0) showed strong diffraction peaks at 2θ=26.92°, 34.22°, 38.22°, and 52.17° corresponding to (110), (101), (200) and (211) crystal faces of rutile structure of $SnO_2$. The anatase structure of $TiO_2$ was identified by the major diffraction peak at 2θ=25.43°. The XRD analysis of the bilayer samples S1, S2 and S3 showed diffraction peaks similar to $SnO_2$ crystal structure and additional peak at 2θ=25.4° corresponding to (101) crystal faces of anatase structure of $TiO_2$ was detected for samples S2 and S3. The XRD analysis of the composite $SnO_2/TiO_2$ structure (S4-S6) revealed three major peaks similar to $SnO_2$ (S0). The position of the major diffraction peak of multilayer oxides shifts slightly from 2θ=26.78° (S6) to 2θ=26.87° (S5) and 2θ=26.91° (S4) with decreasing % vol of $TiO_2$. In addition, the average crystal size of all the samples based on the major diffraction peak was calculated by using the Scherrer formula $$D = \frac{K\lambda}{\beta \cos(\theta)}, \quad (1)$$

where D is the average size of nanocrystals, λ is the X-ray wavelength (1.5056 nm), β is the line broadening at half the maximum peak intensity (FWHM), K=0.9 is a dimensionless shape factor and θ is the major diffraction peak position. The average size of $SnO_2$ (S0) nanocrystals after the annealing process was found to be d=7.87 nm. The characteristic size of nanocrystals for a multilayer $SnO_2/TiO_2$ structure was found to be smaller, compared to pure $SnO_2$: d=4.87 nm (S4), d=4.54 nm (S5) and d=4.09 nm (S6). The crystal size of the $TiO_2$ (S7) was calculated to be 4.21 nm. The smaller grain size of the composite oxides (S4-S6) could be an advantage for gas sensing properties. During the XRD analysis, samples S4-S6 showed no specific peaks correlated to $TiO_2$ crystal structure. However, a noticeable asymmetry as well as a slight shift in the major peak of the multilayer structure in FIG. 23(c) may be attributed to the overlap of $TiO_2$ and $SnO_2$ peaks, caused by the small $TiO_2$ nanocrystals present in the layer.

The morphology of samples S0-S7 was also studied by SEM (Zeiss Supra 35), as shown in FIG. 24. All the samples demonstrated rough and porous polycrystalline structure with short neck-like interconnections between the grains. It can be seen that the porosity of the samples S0-S3 was gradually decreasing with the increasing content of $TiO_2$. The SEM software analysis was used to determine the average grain size of the samples S0-S7. The grain size of the pure $SnO_2$ (S0) and $SnO_2/TiO_2$ (S1-S3) bilayer structures from SEM analysis were found to be in a range of 10-15 nm. The $SnO_2/TiO_2$ (S4-S6) multilayer structure also showed a slight decrease in porosity with increasing of $TiO_2$ content from 5% vol. to 20% vol. The grain size of the multilayer $SnO_2/TiO_2$ structures (S4-S6) was in the range of 5-10 nm. It was found that sample S4 has more uniform grain size distribution and higher porosity in comparison to the rest of the samples. The combination of small grains with high porosity of samples S4, S5 and S6 creates favorable conditions for catalytic reactions thanks to the large surface area and high number of active sites.

Figure 25A:
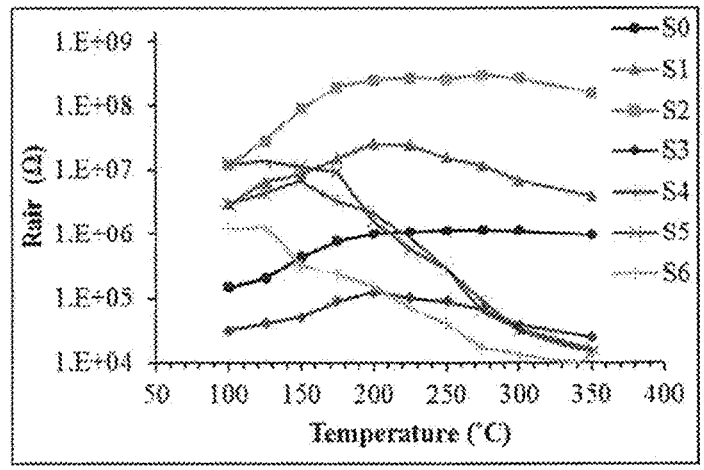
FIGS. 25A-C.
Figure 25B:
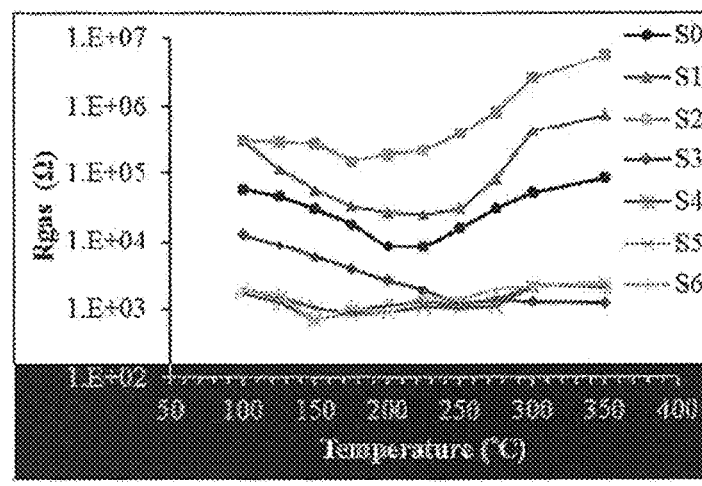
Figure 25C:
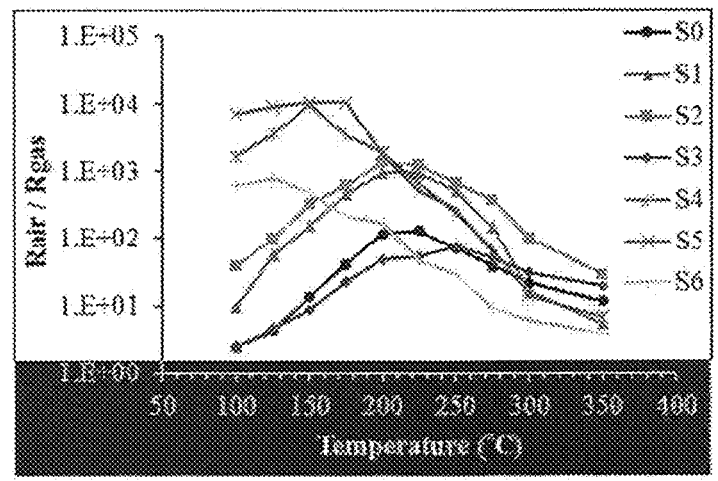

Sensors S0-S7 performance characteristics were first investigated over a wide temperature range of 100-350° C. for exposures to 10 ppm of $H_2S$ in synthetic air (FIG. 25). The optimized temperature conditions for $H_2S$ detection were found for each sensor S0-S6 (Table 3). The pure $TiO_2$ (S7) sample did not show any noticeable response to 10 ppm of $H_2S$ over the temperature range 100-350° C. The bilayer $SnO_2/TiO_2$ structure (S2) demonstrated a much higher response of $1.88 \times 10^3$ to 10 ppm to $H_2S$ gas at lower temperature of 200° C. compared to pure $SnO_2$ (S0) sensitivity of $1.31 \times 10^2$ at 225° C. The highest sensor response to 10 ppm of $H_2S$ of $1.06 \times 10^4$ was observed for $SnO_2/TiO_2$ (S5) composite structure at an even lower temperature of 150° C. It was demonstrated that $SnO_2/TiO_2$ multilayer material has superior sensitivity toward $H_2S$ at lower temperatures (compared to $SnO_2$, $TiO_2$, and the $SnO_2/TiO_2$ bilayers). The sensor performance characteristics of the $SnO_2$ based sensor with 10% vol. of $TiO_2$ (S5) was found to be more efficient compared to the other results from previous reports (Table 1).

The content of $TiO_2$ in the hybrid structure was found to be a crucial parameter that determines sensor performance. Both types of hybrid oxide structures (bilayer and multilayer) demonstrated decline in sensitivity for high contents of $TiO_2$ in the layer. A thick (20 nm) compact layer of $TiO_2$ deposited over the $SnO_2$ layer (S3) affected the layer porosity and caused a decrease in sensor response due to the lack of $SnO_2$ surface exposure to ambient air even at a higher temperature (300° C.). The bilayer structure of $SnO_2$ with 20 nm of $TiO_2$ coating demonstrated very low resistance over the temperature range 100-350C, compared to the other bilayer samples with thinner $TiO_2$ coating. Increasing content of $TiO_2$ within the multilayer structure (S6) from 10 to 20% decreased the sensitivity of the sensor. The sensor S6 with 20% vol. of $TiO_2$ demonstrated low resistance over the temperature range 100-350C and lower sensitivity compared to the other complex oxides with lower $TiO_2$ concentration.

TABLE 3

Optimum operational parameters of sensors S0-S6 upon exposure to 10 ppm of $H_2S$

| Sample | R air ($\Omega$) | R gas ($\Omega$) | R air/R gas | Temperature (° C.) |
|---|---|---|---|---|
| S0 | $1.10 \times 10^{-6}$ | $8.43 \times 10^{-3}$ | $1.31 \times 10^{-2}$ | 225 |
| S1 | $2.53 \times 10^{-7}$ | $2.64 \times 10^{-4}$ | $9.55 \times 10^{-2}$ | 200 |
| S2 | $2.50 \times 10^{-8}$ | $1.85 \times 10^{-5}$ | $1.88 \times 10^{-3}$ | 200 |
| S3 | $8.93 \times 10^{-4}$ | $1.17 \times 10^{-3}$ | $7.60 \times 10^{-1}$ | 250 |
| S4 | $6.90 \times 10^{-6}$ | $6.99 \times 10^{-2}$ | $9.87 \times 10^{-3}$ | 150 |
| S5 | $9.39 \times 10^{-6}$ | $8.82 \times 10^{-2}$ | $1.06 \times 10^{-4}$ | 150 |
| S6 | $3.21 \times 10^{-5}$ | $6.65 \times 10^{-2}$ | $4.83 \times 10^{-2}$ | 150 |

Sensors S2 (bilayer) and S5 (multilayer) demonstrated the highest sensitivity to $H_2S$ in their groups due to the optimized content of $TiO_2$. The bilayer sensor (S2) demonstrated the highest resistance in ambient air among all the sensors (S0-S6), which is an indication of the maximum depletion of carriers in the catalytic layer.

The superior response of the multilayer oxide sensors (S4 and S5), compared to the rest of the sensors, was attributed to the optimal content of $TiO_2$ uniformly distributed through the volume of the catalytic layers affecting the morphological, electrical and catalytic properties of the sensor. Multilayer structures demonstrated smaller average crystal size after the annealing, higher porosity for 5 and 10% vol. of $TiO_2$ and the highest surface roughness across all the sensors.

Based on our studies over a wide temperature range, the pure unmodified $SnO_2$ sensor demonstrated relatively poor $H_2S$ detection capabilities, compared to hybrid (multilayer or bilayer) $SnO_2/TiO_2$ structures. Also, multilayer structures respond better to hydrogen sulfide exposures, than bilayer structures. We relate this phenomenon to the balance between the catalytic activity of the layer and conversion of this catalytic activity into a measurable signal through the charge transfer. The catalytic activity is determined by the surface area of the interactive layer, grain size and structure, and by the number of reaction centers (active sites) in the individual grains. The charge transfer that converts catalytic activity into a measurable signal is determined by the oxygen-induced depletion region underneath the oxide surface and by the multiple heterojunctions between the grains.

A heterojunction is a cleanly lattice-matched interface (grain boundary) that occurs between the nanocrystals of different crystalline materials. These semiconducting materials have unequal electronic band gaps as opposed to a homojunction. A homojunction is a cleanly lattice-matched interface (grain boundary) that occurs between the nanocrystals of the same crystalline materials. Heterojunction manufacturing generally requires the use of molecular beam epitaxy (MBE) or sputtering technologies in order to precisely control the deposition thickness and create a cleanly lattice-matched abrupt interface.

Both Heterojunctions and homojunctions are lattice-matched grain boundaries with strong atomic bonding between the nanograins. Nanograins can be visualized as bricks of a 3-dimensional wall. Obviously, one nanograin can have many grain boundaries (heterojunctions) with the neighboring nanograins. Again, one nanograin is a monocrystal (single-crystal) and a gas sensitive layer is a polycrystalline material. A single-crystal, or monocrystalline, solid is a material in which the crystal lattice of the entire sample is continuous and unbroken to the edges of the sample, with no grain boundaries. A crystalline material consisting of many grains of different orientation (like a ceramic) is called polycrystalline.

When these factors are balanced, they amplify each other as observed in the multilayer oxide structures. In the bilayer structure, the surface depletion was remarkable (even higher than in the multilayer oxides), but the catalytic activity suffered because of the uncontrolled growth of $TiO_2$ grains and their agglomeration, which substantially reduced their catalytic activity.

Figure 26A:
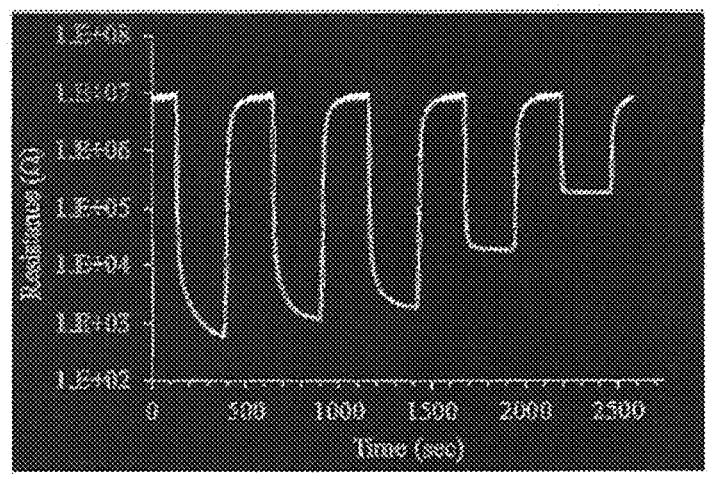
FIGS. 26A-C.
Figure 26B:
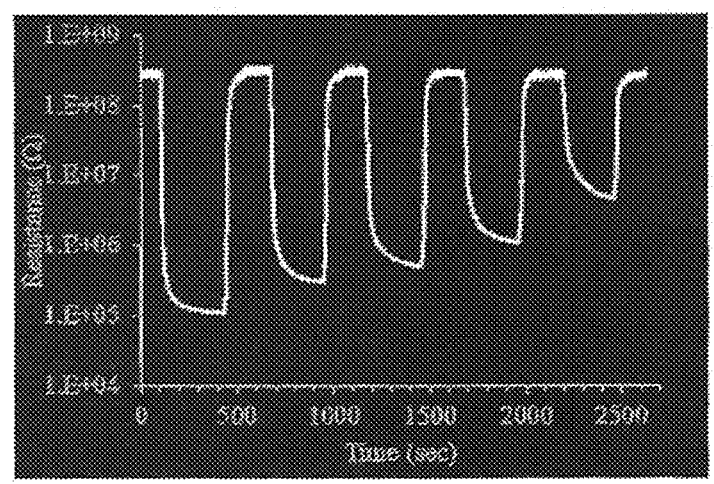
Figure 26C:
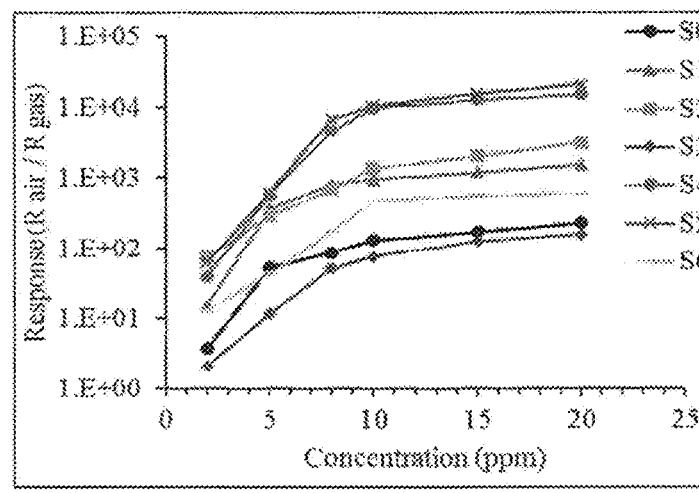

Response and recovery times were found from the sensor response to 10 ppm of $H_2S$ under optimal temperature conditions for each sensor (Table 4). Sensors S2 and S5 demonstrated shortest time for the sensor's response resistance to reach 90% of its steady state value (FIG. 26).

TABLE 4

Response and recovery time of sensors S0-S6 to 10 ppm of $H_2S$

| Sample number | Response time $T_{90}$ (sec) | Recovery time $T_{90}$ (sec) | Concentration (ppm) | Temperature (° C.) |
|---|---|---|---|---|
| S0 | 3.7 | 5.6 | 10 | 225 |
| S1 | 3.5 | 2.8 | 10 | 200 |
| S2 | 3.3 | 2.5 | 10 | 200 |
| S3 | 3.7 | 2.9 | 10 | 250 |
| S4 | 3.0 | 2.4 | 10 | 150 |
| S5 | 3.2 | 2.4 | 10 | 150 |
| S6 | 3.9 | 2.7 | 10 | 150 |

Figure 27A:
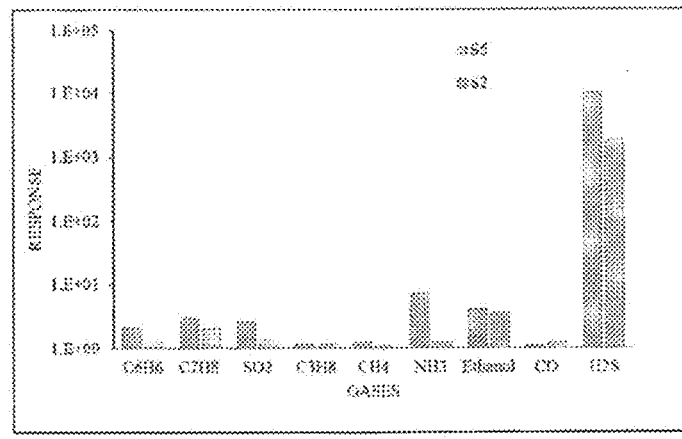
FIGS. 27A-B.
Figure 27B:
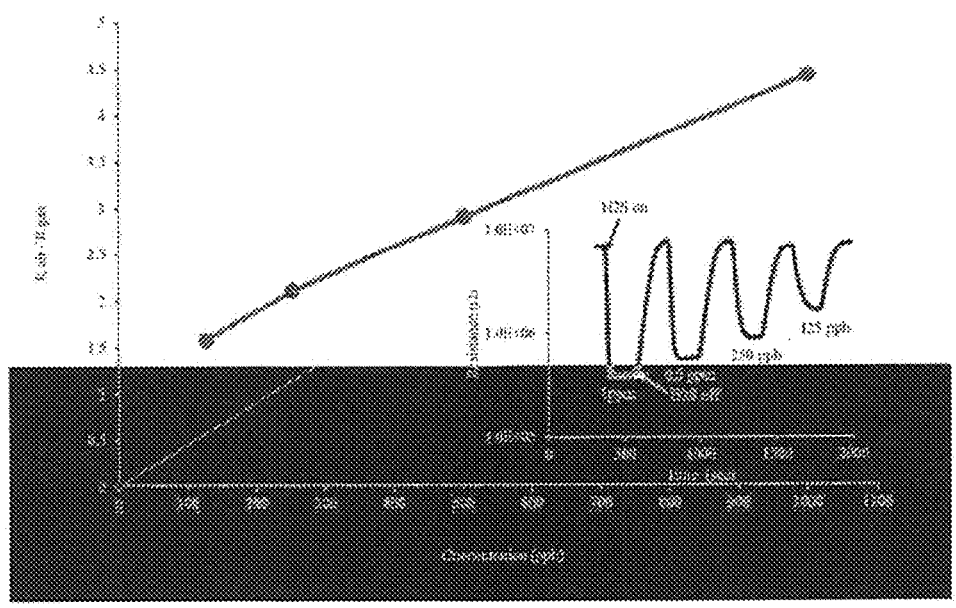

Besides excellent sensitivity, quick response and recovery time (Table 4), hybrid sensors also demonstrated superior selectivity to hydrogen sulfide. In our experiments, hybrid sensors were capable of detecting hydrogen sulfide in complex gas mixtures, such as natural gas, which is not typical for metal oxide sensors. The illustration of cross-sensitivity studies on hybrid sensors is shown in the FIG. 27. FIG. 27(a) shows the response amplitudes of sensors S5 (multilayer structure) and S2 (bilayer structure) to various gases at different concentrations. FIG. 27(b) shows the response of sensor S5 to sub-ppm concentrations of $H_2S$ diluted in pure methane. We attribute this remarkable selectivity of hybrid layers to high catalytic activity of $SnO_2/TiO_2$ hybrid structures relative to $H_2S$ at relatively low temperatures. Maximum sensor response for bilayer and multilayer structures was achieved at 200° C. and 150° C. respectively, which is substantially lower than the optimum activation temperature of pure tin dioxide sensor (300° C.). It is related to a lower activation temperature for oxidation of hybrid catalyst, compared to tin dioxide. Because of that, the energy of active sites on the surface was not enough to overcome the activation barrier of combustibles, ethanol and carbon dioxide, which provides a natural cut-off for all the catalytic reactions except for the $H_2S$ decomposition and oxidation.

The major factor that determines chemical sensitivity of a metal oxide sensor is its catalytic activity toward the analyte of interest. Nanoscale titanium dioxide is a very reactive catalyst for the Clauss process and interacts with hydrogen sulfide more efficiently than tin dioxide. Multiple reports show that materials demonstrate their maximum catalytic activity in the nanoparticle form, which is related to maximization of the surface area and the number of active sites (reaction centers). In our experiments, both double layer and multilayer-type sensors demonstrated maximum sensitivity at a certain volume percentage of titanium dioxide in the tin dioxide layer. The pure tin dioxide sensor demonstrated moderate sensitivity and no selectivity to hydrogen sulfide. Also, a long time of recovery after the exposure is evidence of a relatively low catalytic reaction rate. With an increase of titanium oxide content in the hybrid layer, sensitivity increased dramatically and recovery time dropped to a few seconds. Our tests showed the highest sensitivity and the fastest recovery at 10% vol of titanium oxide. Further increase of titanium oxide content caused the decline of sensor performance, which is associated with agglomeration of titanium nanoparticles into larger grains and reduction of their catalytic activity. Substantial increase in titanium oxide content, overcoming its percolation threshold and formation of a continuous titanium dioxide matrix, created an inert film with no catalytic properties and poor electrical conductivity.

The present invention is distinguishable from currently available technology such as that represented by US Pub 2014/0138259 by Mickelson, and Leary (U.S. Pat. No. 4,453,151 by Leary. For example, in U.S. Pat. No. 4,453,151, describes a spray pyrolysis method of sensor fabrication comprises spray deposition of a mixture of metal oxides mixed together with various metal and non-metal materials which serve in the finished product as activators, dopants, and/or film binder materials, and including in suspension a molecular sieve material, for enhancing and defining porosity on a scale of molecular dimensions in the finished sensor. All of the foregoing materials are suspended in a suitable solution and preferably sprayed onto a heated insulating substrate to form the finished product.

The spray pyrolysis method is a chemical method of synthesis from precursors (typically salts), where all precursor materials are deposited on a heated substrate in aerosol form concurrently, producing a uniform film. Nucleation occurs in the solvent followed by solvent evaporation. However, growth conditions for different components of the mixture is different, meaning that temperature of the substrate, pressure in the reactor, gas temperature and flow rate in the reactor etc. are different for Ti, TiO2, Au, Cu, CuO, Cu2O, Mo, MoO2, MoO3, Ni, NiO, Ni2O3, Pt, Pd, Ag, AgO, Ru, RuO2, Rh, Rh2O3, Os, OsO2, OsO4, Ir, IrO2, etc. nanocrystals. Since all the precursors are deposited on the substrate simultaneously, the parameters of synthesis for several different nanocrystals at the same time cannot be controlled. The major disadvantages of spray pyrolysis methods for hybrid nanomaterials result from difficulties with determining growth temperature and difficulties with scaling-up (yield is very low). This causes difficulties in spray pyrolysis for the mass production of chemical sensors.

This is not a problem for physical methods, such as sputtering, a reference to which is now included in the amended claims. In the present invention the metal oxide and dopant layers are applied by sputtering which is a bottom-up approach in which the nanograins self-assemble. The grain size is directly proportional to the deposited layer thickness. In summary, U.S. Pat. No. 4,453,151 method cannot provide precise control over the grain size of chemically different nanocrystals in the hybrid polycrystalline material, Applicant's method can. Leary does not teach precise grain control, as now supported by Applicant's claims.

In addition, US Pub 2014/0138259 by Mickelson utilizes post synthesis deposition of metal oxide nanoparticles, meaning that the nanoparticles are synthesized, added to a solvent and then the mixture (suspension) is deposited on platinum leads using a micro-pipette. This method is the above described "sol-gel deposition". US Pub 2014/0138259 specifically discloses "deposition of nanoparticles". The layer formed by sol-gel deposition is not a continuous material, but a collection of particles glued together by some molecular binding agent. Post-synthesis deposition of droplets (US Pub 2014/0138259) can never produce a layer with a uniform and precisely controlled thickness and shape. This is natural for droplets because they are highly non-uniform.

Applicant deposits materials from individual atoms under high vacuum as continuous layers using a sputtering technique. After that Applicant anneals the continuous structure, so that it re-crystallizes and transforms into a hybrid polycrystalline material, which is essentially a collection of millions of nanoscale grains or nanoscale crystals of one or more crystalline material electrically and mechanically connected through a cleanly lattice-matched interface called a heterojunction for a hybrid polycrystalline material. Mickelson's gas-sensitive materials are artificially created utilizing a top-down approach. The present invention uses gas-sensitive materials are naturally grown utilizing a bottom-up approach to create uniform droplets and layers of material of a thickness between 10-200 nm.

Applicant believes US Pub 2014/0138259 is not relevant because US Pub 2014/0138259 is merely mixing powders together forming a paste and then baking the paste to harden the material. Applicant's material is a hybrid polycrystalline structure, where individual nanocrystals are grown together as a continuous layer. The grains of different materials are electrically and mechanically connected to each other forming heterojunctions. Heterojunctions are only formed when lattice-matched interfaces between the nanocrystals of different materials are achieved during the synthesis. For US Pub 2014/0138259 post-synthesis deposition of powder-based material, heterojunctions are not formed because there is no lattice matching between the individual particles. These include crystalline metal oxides, metals and non-metals.

In addition, US Pub 2014/0138259 does not teach the concept of a primary oxide as described herein. For example, there are multiple discrepancies with US Pub 2014/0138259 structures. First, the powder of microparticles that US Pub 2014/0138259 is using for layer fabrication was obtained from shredding and milling bulk oxide material (top-down approach) and Applicant's nanograins are self-assembled from individual atoms (bottom-up approach). It is well-known that the physical and chemical properties of top-down and bottom-up nanocrystals are very different, even if they have the same size. Also, the homojunctions formed between the nanocrystals during the self-assembly provide much more efficient charge transfer between them thanks to a lattice-matched interface. Efficient charge transfer is essential for high sensitivity but cannot be achieved for post-synthesis deposition of metal oxide paste (US Pub 2014/0138259).

Numerous modifications and variations of the present invention are possible in light of the above teachings. It is therefore to be understood that within the scope of the appended claims, the invention may be practiced otherwise that as specifically described herein.

What is claimed is:

1. A chemical sensor platform, comprising:
   (a) an oxidized silicon membrane, comprising a silicon (Si) layer and a silicon oxide ($SiO_2$) layer, wherein the $SiO_2$ layer is located on top of the silicon layer and, comprises: a plurality of separate sensor areas;
   (b) at least one heating element in contact with the $SiO_2$ layer and located near at least one edge of each sensor area;
   (c) a plurality of pairs of interdigitated electrical leads, each in contact with the $SiO_2$ layer, wherein one pair of electrical leads is at least partly located on each of the separate sensor areas;
   (d) a plurality of metal oxide layers wherein one of the plurality of metal oxide layers is located on each of the plurality of sensor areas and is in contact with at least a part of the pair of interdigitated electrical leads located on the same area, said plurality of metal oxide layers comprising self-assembled metal oxide nanograins and homojunctions between the nanograins on each layer's surface;
   (e) a plurality of uniform dopant layers comprising nanoparticles wherein the said plurality of dopant layers is arranged in contact with the surface of at least one metal oxide layer, wherein the said plurality of dopant layers is between 10-200 nm thick; and
   (f) multiple heterojunctions comprising lattice-matched interfaces between the metal oxide nanograins and at least one dopant layer of the plurality of dopant layers comprising nanoparticles to form an electrically and physically integrated hybrid polycrystalline structure.

2. The chemical sensor platform of claim 1, wherein the membrane, further comprises: a plurality of $Si/SiO_2$ connectors.

3. The chemical sensor platform of claim 1, wherein the membrane, further comprises: 4 $Si/SiO_2$ connectors.

4. The chemical sensor platform of claim 1, wherein each of the metal oxide-layers is $SnO_2$.

5. The chemical sensor platform of claim 1, wherein each of the dopant layers is independently selected from at least one of: $TiO_2$, Au, Cu, Mo, Ni, Pt, Pd, and Ag.

6. The chemical sensor platform of claim 1, wherein each of the dopant layers is $TiO_2$.

7. A multilayer chemical sensor, comprising:
   (a) an oxidized silicon membrane comprising: a silicon (Si) layer; and a silicon oxide ($SiO_2$) layer, wherein the $SiO_2$ layer is located on top of the silicon layer and, comprises: a sensor area;
   (b) a heating element in contact with the $SiO_2$ layer and located near at least one edge of the sensor area;
   (c) one pair of interdigitated electrical leads in contact with the $SiO_2$ layer and at least partly located on the sensor area; and
   (d) a sensing layer comprising: a plurality of alternating uniform layers, wherein each uniform layer of the plurality of alternating uniform layers comprises a metal oxide layer and a dopant layer, wherein each metal oxide layer is between 5-40 nm thick, and wherein each dopant layer is between 2-15 nm thick, wherein each of the metal oxide layers comprises self-assembled metal oxide nanograins and homojunctions between the nanograins on the metal oxide layer's surface and each of the dopant layers comprises nanoparticles and each dopant layer is arranged in contact with the surface of one metal oxide layer, and multiple heterojunctions comprising lattice-matched interfaces between the metal oxide nanograins and the dopant nanoparticles to form an electrically and physically integrated hybrid polycrystalline structure; and
   wherein the sensing layer is located on the sensor area and at least one metal oxide layer is in contact with at least a part of the pair of interdigitated electrical leads and the $SiO_2$ layer.

* * * * *